(12) United States Patent
Mouri

(10) Patent No.: US 8,984,955 B2
(45) Date of Patent: Mar. 24, 2015

(54) METHOD OF ARRESTING FATIGUE CRACK GROWTH IN METAL MEMBER, AND FATIGUE CRACK GROWTH-ARRESTED METAL MEMBER

(71) Applicant: IHI Corporation, Koto-ku (JP)

(72) Inventor: Masashi Mouri, Tokyo (JP)

(73) Assignee: IHI Corporation, Koto-ku (JP)

( * ) Notice: Subject to any disclaimer, the term of this patent is extended or adjusted under 35 U.S.C. 154(b) by 0 days.

(21) Appl. No.: 14/257,041

(22) Filed: Apr. 21, 2014

(65) Prior Publication Data

US 2014/0224032 A1   Aug. 14, 2014

Related U.S. Application Data

(63) Continuation of application No. PCT/JP2012/077407, filed on Oct. 24, 2012.

(30) Foreign Application Priority Data

Oct. 27, 2011 (JP) .................................. 2011-235961

(51) Int. Cl.
*G01N 3/00* (2006.01)
*G01N 19/08* (2006.01)
*G01N 29/04* (2006.01)
*G01N 3/08* (2006.01)
*B23P 6/04* (2006.01)

(52) U.S. Cl.
CPC ... *G01N 3/08* (2013.01); *B23P 6/04* (2013.01); *G01N 2203/0062* (2013.01)
USPC .............................................. 73/788; 73/799

(58) Field of Classification Search
USPC .................................................... 73/788, 799
See application file for complete search history.

(56) References Cited

U.S. PATENT DOCUMENTS

2007/0050963 A1*  3/2007  Keller .................... 29/402.12
2008/0052014 A1*  2/2008  Toyosada .................... 702/34

FOREIGN PATENT DOCUMENTS

| JP | 03-213216 A | 9/1991 |
| JP | 2010-125534 A | 6/2010 |
| JP | 2011-106181 A | 6/2011 |

OTHER PUBLICATIONS

International Search Report issued on Jan. 29, 2013 for PCT/JP2012/077407 filed on Oct. 24, 2012 with English translation.
International Written Opinion issued on Jan. 29, 2013 for PCT/JP2012/077407 filed on Oct. 24, 2012.

* cited by examiner

*Primary Examiner* — Lisa Caputo
*Assistant Examiner* — Jamel Williams
(74) *Attorney, Agent, or Firm* — Oblon, McClelland, Maier & Neustadt, L.L.P.

(57) ABSTRACT

In a method of arresting fatigue crack growth in a metal member, a hole is formed beside a tip portion of a fatigue crack with respect to a crack extension direction, in a metal member body, in which the fatigue crack occurs due to an action of applied cyclic tensile stress. Then, a press-fit object being higher in stiffness than the metal member body and larger in external size than the hole is press-fitted into the hole. Compressive stress is made to act on the tip portion of the fatigue crack from directions lateral to the crack extension direction.

14 Claims, 18 Drawing Sheets

METHOD OF ARRESTING FATIGUE CRACK GROWTH IN METAL MEMBER, AND FATIGUE CRACK GROWTH-ARRESTED METAL MEMBER

CROSS REFERENCE TO RELATED APPLICATIONS

This application is a continuation application of International Application No. PCT/JP2012/77407, filed on Oct. 24, 2012, which claims priority to Japanese Patent Application No. 2011-235961, filed on Oct. 27, 2011, the entire contents of which are incorporated by references herein.

BACKGROUND OF THE INVENTION

1. Field of the Invention

The present invention relates to a method of arresting fatigue crack growth in a metal member, and a fatigue crack growth-arrested metal member. The present invention relates to: a method of arresting fatigue crack growth in a metal member which is aimed at arresting growth of a fatigue crack occurring in a metal member used for any of a bridge, a ship, a crane and the like; and the metal member in which the fatigue crack growth is arrested.

2. Description of the Related Art

A stop-hole method has been used to arrest growth of a fatigue crack occurring in a metal member used for any of a bridge, a ship, a crane and the like. The stop-hole method is a method of arresting a fatigue crack by relaxing stress concentration at a fatigue crack tip by use of a round hole which is provided to the crack tip in such a manner as to connect with the crack.

Another fatigue crack growth arresting method is to arrest the growth of a fatigue crack by closing the fatigue crack in a surface portion through a peening process or the like on the crack surface, as shown in Japanese Patent Application Publication No. 2011-106181 (Patent Literature 1) and Japanese Patent Application Publication No. 2010-125534 (Patent Literature 2).

SUMMARY OF THE INVENTION

Although the stop-hole method can temporarily relax the stress concentration by providing the round hole to the fatigue crack tip, another fatigue crack is likely to occur and grow from the round hole as a stop-hole due to the action of repeatedly applied stress. The method of closing the fatigue crack through the peening process or the like on the crack surface has a difficulty in closing a fatigue crack inside the metal member in the plate-thickness direction, and there remains a possibility that the fatigue crack may grow further.

With this taken into consideration, an object of the present invention is to provide: a method of arresting fatigue crack growth in a metal member which is capable of further arresting growth of a fatigue crack occurring in a metal member; and a metal member in which fatigue crack growth is arrested.

Solution to Problem

A method of arresting fatigue crack growth in a metal member according to the present invention, comprises: a hole forming step of forming a hole in a metal member body in which a fatigue crack occurs due to an action of applied cyclic tensile stress, the hole arranged beside a tip portion of the fatigue crack with respect to a crack extension direction; and a press-fitting step of making compressive stress act on the tip portion of the fatigue crack from a direction lateral to the crack extension direction by press-fitting a press-fit object into the hole, the press-fit object being higher in stiffness than the metal member body and larger in external size than the hole.

In the method of arresting fatigue crack growth in a metal member according to the present invention, in the hole forming step, the hole is formed in a way that a straight line joining the center of the hole and a tip of the fatigue crack is orthogonal to the crack extension direction.

In the method of arresting fatigue crack growth in a metal member according to the present invention, in the hole forming step, a stress concentration area caused by stress concentration on the tip portion of the fatigue crack is found beforehand, and the hole is formed in a location outside the stress concentration area.

In the method of arresting fatigue crack growth in a metal member according to the present invention, in the hole forming step, the hole is formed in the location around the tip portion of the fatigue crack, and between the crack extension direction and a direction at an angle $\theta$ to the crack extension direction, and the angle $\theta$ is given by a stress analysis.

In the method of arresting fatigue crack growth in a metal member according to the present invention, the angle $\theta$ is 55 degrees when uniform tensile stress is made to act in a direction orthogonal to the crack extension direction.

In the method of arresting fatigue crack growth in a metal member according to the present invention, in the hole forming step, the hole is formed in a location where the shortest distance between a peripheral edge of the hole and the tip portion of the fatigue crack is 1 mm or longer in order to prevent the hole and the tip portion of the fatigue crack from connecting with each other when the press-fit object is press-fitted into the hole.

In the method of arresting fatigue crack growth in a metal member according to the present invention, in the hole forming step, the hole is formed in each of locations symmetrical with respect to the tip portion of the fatigue crack in a direction orthogonal to the crack extension direction.

In the method of arresting fatigue crack growth in a metal member according to the present invention, the fatigue crack penetrates the metal member body in its thickness direction, the hole is formed penetrating the metal member body in its thickness direction, and the press-fit object is formed with a length equal to or longer than that of the hole.

In the method of arresting fatigue crack growth in a metal member according to the present invention, the press-fit object includes a press-fit portion to be press-fitted into the hole, and a head portion provided on one end side of the press-fit portion, and being larger in external size than the press-fit portion. Moreover, the head portion of the press-fit object is provided with any one of a flange, a screw thread and a groove.

A fatigue crack growth-arrested metal member of the present invention, includes: a hole formed in a metal member body in which a fatigue crack occurs due to an action of applied cyclic tensile stress, and provided beside a tip portion of the fatigue crack with respect to a crack extension direction; and a press-fit object being higher in stiffness than the metal member body and larger in external size than the hole, and configured to make compressive stress act on the tip portion of the fatigue crack from a direction lateral to the crack extension direction by being press-fitted into the hole.

In the fatigue crack growth-arrested metal member according to the present invention, the hole is formed in a way that a straight line joining the center of the hole and a tip of the fatigue crack is orthogonal to the crack extension direction.

In the fatigue crack growth-arrested metal member according to the present invention, the hole is formed in a location outside a stress concentration area caused by stress concentration on the tip portion of the fatigue crack.

In the fatigue crack growth-arrested metal member according to the present invention, the hole is formed in the location around the tip portion of the fatigue crack, and between the crack extension direction and a direction at an angle θ to the crack extension direction, and the angle θ is given by a stress analysis.

In the fatigue crack growth-arrested metal member according to the present invention, the angle θ is 55 degrees when uniform tensile stress is made to act in a direction orthogonal to the crack extension direction.

In the metal member which includes the fatigue crack caused by the action of the applied cyclic tensile stress, the foregoing configurations enable the compressive stress to act on the tip portion of the fatigue crack sideways to the crack extension direction, and accordingly make it possible to further arrest the fatigue crack growth in the metal member.

DESCRIPTION OF THE EMBODIMENTS

Figure 1A:
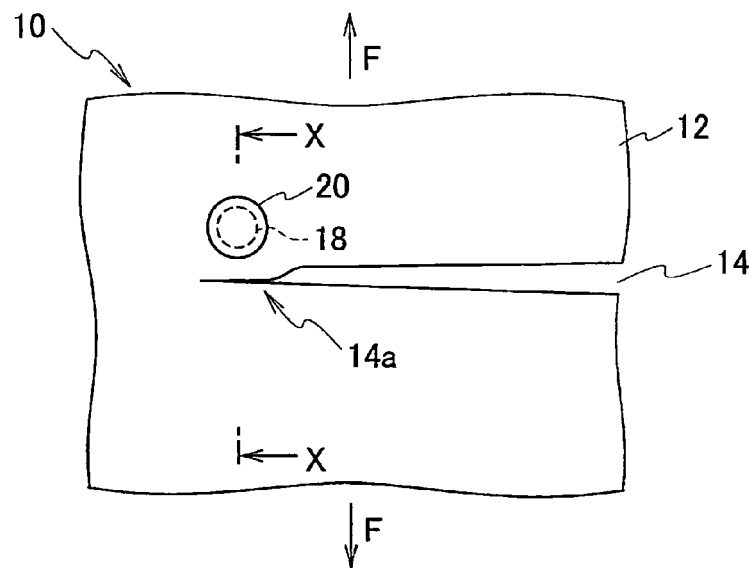
FIG. 1A is a plan view showing the structure of the metal member in which the fatigue crack is arrested in the embodiment of the present invention.
Figure 1B:
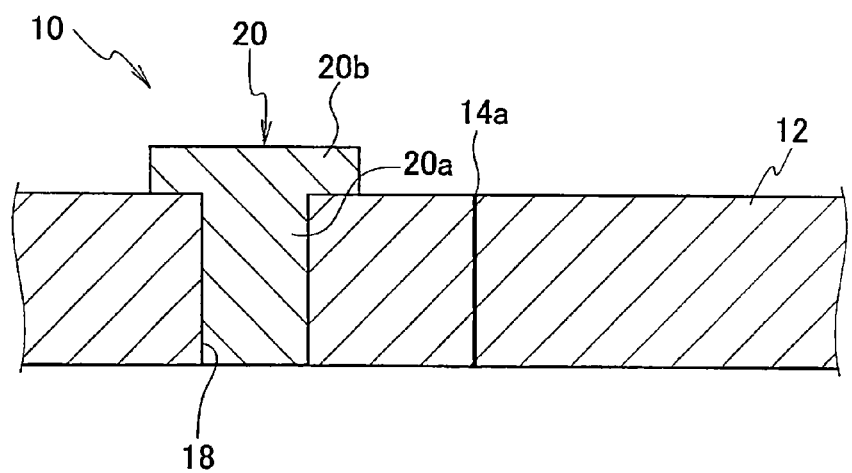
FIG. 1B is a cross-sectional view taken along the X-X direction indicated in FIG. 1A in the embodiment of the present invention.

Detailed descriptions will be hereinbelow provided for an embodiment of the present invention by use of the drawings. FIG. 1A is a plan view showing the structure of the metal member 10 in which the fatigue crack is arrested. FIG. 1B is a cross-sectional view taken along the X-X direction indicated in FIG. 1A.

An action of applied cyclic tensile stress F induced by fatigue loading has caused a fatigue crack 14 in a metal member body 12 in a direction orthogonal to a stress direction of the applied cyclic tensile stress F. The fatigue crack 14 formed, for example, penetrating the metal member body 12 in its thickness direction. Such a fatigue crack 14 grows with accumulation and the like of repeatedly applied plastic strain at a tip portion 14a of the fatigue crack 14 due to the action of the applied cyclic tensile stress F.

Examples of the metal member body 12 include steel-made metal structural members used for bridges, ships, cranes and the like. Such steel-made metal structural members are formed from rolled steel materials for general structural, rolled steel materials for welded structures, and the like. The thickness of the metal member body 12 is approximately in a range of 1 mm to 20 mm, for example.

A hole 18 extending in the thickness direction of the metal member body 12 is formed beside the tip portion 14a of the fatigue crack 14 with respect to the crack extension direction. The hole 18 is formed, for example, penetrating the metal member body 12 in its thickness direction. The shape of the hole 18 may be any of a round hole, a square hole, and the like. In addition, one or multiple holes 18 may be provided. Furthermore, the hole 18 may be formed as a closed-end hole extending in the thickness direction of the metal member body 12.

A press-fit object 20 is press-fitted in the hole 18. The press-fit object 20 is made from a material which is higher in stiffness than that of the metal member body 12. When the metal member body 12 is made from a steel material, the press-fit object 20 is made from a material which is higher in compressive elasticity and hardness (Vickers hardness, for example) than the steel material, and which is less likely to cause plastic deformation, cracking, buckling, and the like as a consequence of press-fitting. Examples of such materials include WC (tungsten carbide)-based cemented carbide, and the like.

The press-fit object 20 includes a press-fit portion 20a which is formed larger in external size than that of the hole 18, and which is to be press-fitted into the hole 18. The press-fit portion 20a is shaped like a column such as a circular column or a square column. When the press-fit portion 20a is shaped like a circular column, the outer diameter of the press-fit portion 20a is in a range of 3 mm to 5 mm, for example.

The press-fit portion 20a may be formed equal to or longer than the length of the hole 18. Nevertheless, the press-fit portion 20a may be formed shorter than the length of the hole 18. The length of the press-fit portion 20a is in a range of 5 mm to 20 mm, for example. In addition, for the purpose of making it easier to drive the press-fit object 20 into the hole 18, a head portion 20b larger in external size than the press-fit portion 20a may be provided at one end of the press-fit portion 20a in its longitudinal direction.

Figure 2:
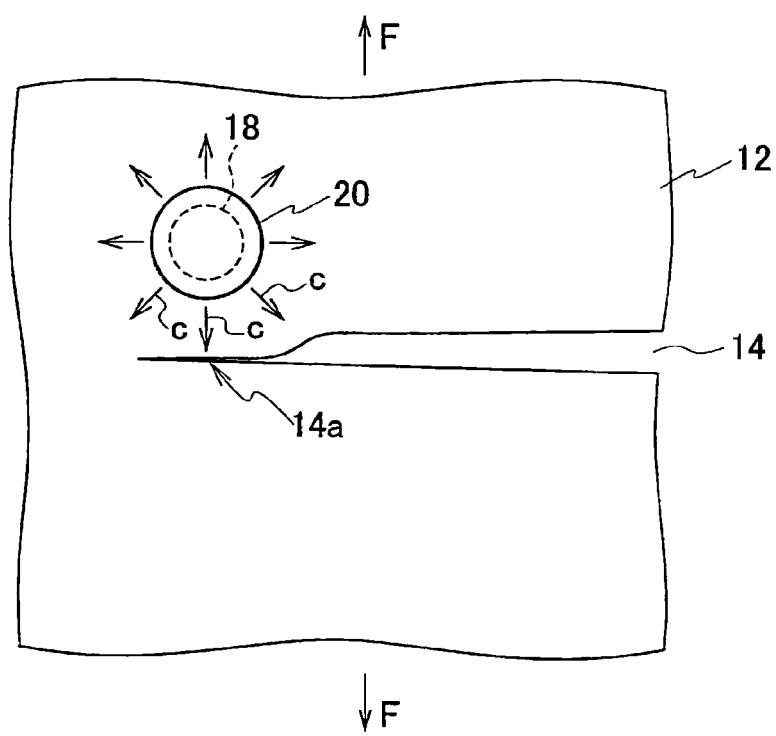
FIG. 2 is a plan view showing an action of the metal member in which the fatigue crack growth is arrested in the embodiment of the present invention.

FIG. 2 is a plan view showing an action of the metal member 10 in which the fatigue crack growth is arrested. Compressive stress C acts on the tip portion 14a of the fatigue crack 14 from directions lateral to the crack extension direction when the press-fit object 20 is press-fitted into the hole 18 formed in the metal member body 12. An opening in the tip portion 14a of the fatigue crack 14 can be pressed and closed by use of the compressive stress C.

Furthermore, even when the applied cyclic tensile stress F acts on the metal member body 12, part or all of the applied cyclic tensile stress F is canceled out by the compressive stress C acting from the directions lateral to the crack extension direction. For this reason, the expansion of the opening in the tip portion 14a of the fatigue crack 14 can be arrested, and accordingly, plastic deformation of the tip portion 14a of the fatigue crack 14 can be arrested. Thereby, the growth of the fatigue crack 14 is arrested.

Figure 3:
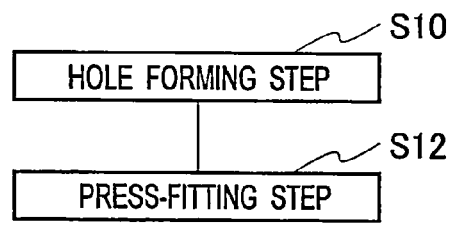
FIG. 3 is a flowchart showing a method of arresting fatigue crack growth in a metal member in the embodiment of the present invention.

Next, descriptions will be provided for a fatigue crack growth arresting method for the metal member. FIG. 3 is a flowchart showing the fatigue crack growth arresting method for the metal member. The fatigue crack growth arresting method for the metal member includes: a hole forming step (S10) of forming the hole 18 in the metal member body 12 in which the fatigue crack 14 has occurred; and a press-fitting step (S12) of press-fitting the press-fit object 20 into the hole 18.

The hole forming step (S10) is a step of forming the hole 18, beside the tip portion 14a of the fatigue crack 14 with respect to the crack extension direction, in the metal member body 12 in which the fatigue crack 14 occurs due to the action of the applied cyclic tensile stress F.

Figure 4:
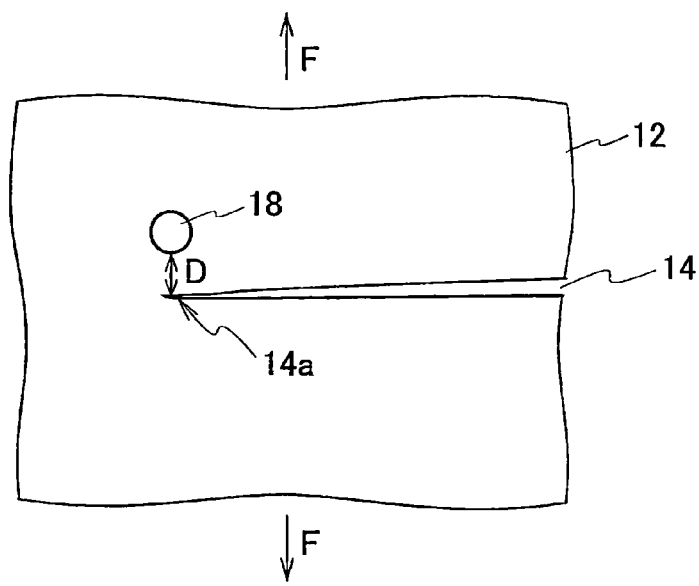
FIG. 4 is a plan view showing a state where a hole is formed in a metal member body in which a fatigue crack has occurred in the embodiment of the present invention.

FIG. 4 is a plan view showing a state where the hole 18 is formed in the metal member body 12 in which the fatigue crack 14 has occurred. The hole 18 is formed beside the tip portion 14a of the fatigue crack 14 with respect to the crack extension direction in order to cause the compressive stress to act on the tip portion 14a of the fatigue crack 14 from the directions lateral to the crack extension direction when the press-fit object 20 is press-fitted into the hole 18. The hole 18 is formed, for example, by being bored in the metal member body 12 with a drill or the like.

Moreover, the hole 18 is formed in a location which does not allow the hole 18 and the tip portion 14a of the fatigue crack 14 to connect with each other when the press-fit object 20 is press-fitted into the hole 18. For the purpose of preventing the hole 18 and the tip portion 14a of the fatigue crack 14 from connecting with each other, the hole 18 may be formed in a location which makes the shortest distance D between the peripheral edge of the hole 18 and the tip portion 14a of the fatigue crack 14 equal to or greater than 1 mm, for example. It should be noted that for the purpose of making larger compressive stress act on the tip portion 14a of the fatigue crack 14, the shortest distance D from the tip portion 14a of the fatigue crack 14 may be not less than 1 mm but not greater than 2 mm.

When the hole 18 is a round hole, the hole 18 may be formed in a way that the straight line joining the center of the hole 18 and the tip of the fatigue crack 14 is orthogonal to the crack extension direction. The forming of the hole 18 in such a location makes it possible to make larger compressive stress act on a tip side of the tip portion 14a of the fatigue crack 14 from the directions lateral to the crack extension direction when the press-fit object 20 is press-fitted into the hole 18.

Figure 5:
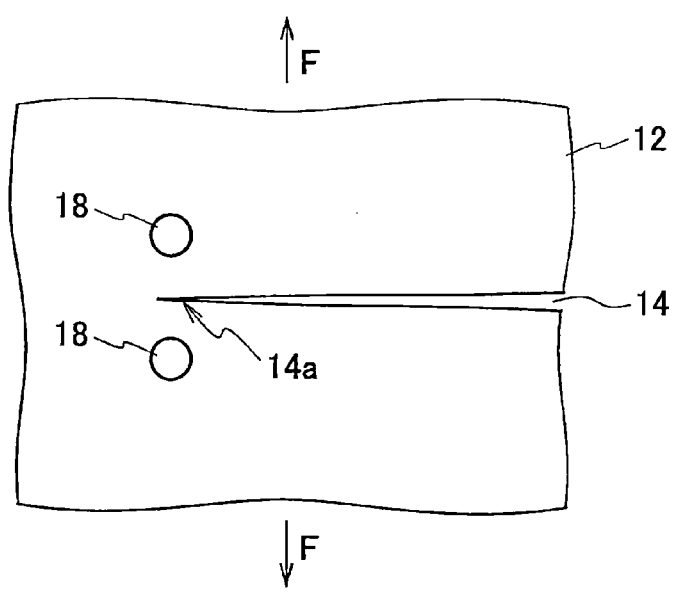
FIG. 5 is a plan view showing a state where two holes are formed in locations symmetrical with respect to a tip portion of the fatigue crack in a direction orthogonal to a crack extension direction in the embodiment of the present invention.

When multiple holes 18 are to be formed, all the multiple holes 18 may be formed on only one side in the crack extension direction. Alternatively, the multiple holes 18 may be formed on both of the one and the other sides to the crack extension direction. Meanwhile, the holes 18 may be respectively formed in locations symmetrical with respect to the tip portion 14a of the fatigue crack 14 in a direction orthogonal to the crack extension direction. FIG. 5 is a plan view showing a state where two holes 18 are formed in locations orthogonally symmetrical with respect to the crack extension direction of the tip portion 14a of the fatigue crack 14. The formation of the holes 18 in such locations can cause the compressive stress to act on the same position of the tip portion 14a of the fatigue crack 14 from both of the one and the other sides to the crack extension direction. It is a matter of course that the locations of the respective holes 18 are not limited to the locations symmetrical with respect to the crack extension direction of the tip portion 14a of the fatigue crack 14 in the direction orthogonal to the crack extension direction.

In the hole forming step (S10), a stress concentration area caused by stress concentration on the tip of the fatigue crack 14 may be found in advance, and the holes may be formed in locations outside the stress concentration area thus found in advance.

Figure 6:
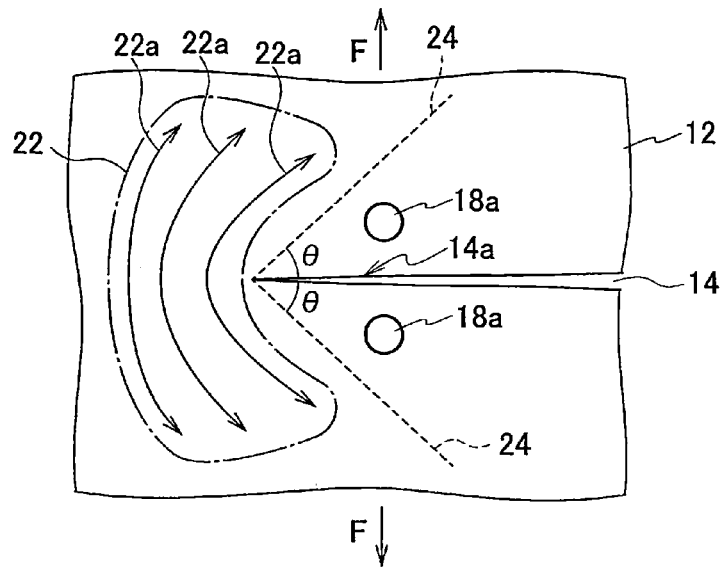
FIG. 6 is a plan view showing a method of forming holes while avoiding a stress concentration area which is caused by stress concentration on the tip of the fatigue crack in the embodiment of the present invention.

FIG. 6 is a plan view showing a method of forming holes 18a while avoiding a stress concentration area 22 which is caused by stress concentration on the tip of the fatigue crack 14. Stress concentration causes the stress concentration area 22, where tensile stress is larger than in the other area, around the tip of the fatigue crack 14. Arrows 22a in the stress concentration area 22 represent their respective lines of stress (flows of stress). In a region around the tip of the fatigue crack 14, the stress concentration area 22 is defined as an area which exerts tensile stress larger than uniform tensile stress when the uniform tensile stress is made to act on the metal member body 12.

The stress concentration area 22 is given in advance by a stress analysis or by measuring stress in an experiment. The stress analysis uses a general finite element method (FEM) or the like. The experiment can use: the measurement of stress distribution by use of X-rays or the like; the measurement of stress distribution by use of a strain gauge; or the like.

The holes 18a are formed while avoiding the stress concentration area 22 which has been given in advance by the stress analysis or by measuring the stress in the experiment. As clear from the lines 22a of stress in the stress concentration area 22, the stress acting on the vicinity of the tip portion 14a of the fatigue crack 14 circumvents the tip of the fatigue crack 14. For this reason, almost none of the applied cyclic tensile stress F acts on the location around the tip portion 14a of the fatigue crack 14 except for the stress concentration area 22.

When the compressive stress is made to act on the tip portion 14a of the fatigue crack 14 from the directions lateral to the crack extension direction by press-fitting the press-fit objects 20 into the holes 18a, an amount of tensile stress canceled out by the compressive stress is small, since as described above, almost none of the applied cyclic tensile stress F acts on the location around tip portion 14a of the fatigue crack 14 except for the stress concentration area 22. Accordingly, the tensile stress will never serve as a driving force to grow the crack.

When part or all of the holes 18 are included in the stress concentration area 22, the peripheral edge of any of the holes is more likely to become a starting point for occurrence of a new crack because a stress level is high at the tip of the fatigue crack 14 due to the stress concentration. However, if the holes 18a are formed while avoiding the stress concentration area 22, the occurrence of a new crack can be arrested.

In order to form the holes 18a while avoiding the stress concentration area 22, the holes 18a may be formed respectively in locations around the tip portion 14a of the fatigue crack 14, as well as between the crack extension direction and directions at an angle θ to the crack extension direction. To this end, the angle θ may be given by a stress analysis. For example, when uniform tensile stress is made to act on far regions in the directions orthogonal to the crack extension direction, the holes 18a may be formed respectively in areas around the tip portion 14a of the fatigue crack 14, as well as between the crack extension direction and the directions 24 at the angle θ of 55 degrees to the crack extension direction. As shown in examples to be described later, it has been given from a stress analysis using the finite element method (FEM) that, when uniform tensile stress is made to act in the directions orthogonal to the crack extension direction, the holes 18a can be formed while avoiding the stress concentration area 22, which is caused by the stress concentration, by forming the holes 18a respectively in the areas around the tip portion 14a of the fatigue crack 14, as well as between the crack extension direction and the directions at the angle θ of 55 degrees to the crack extension direction.

It should be noted that when the stress level of the applied cyclic tensile stress F varies, the stress level varies within the stress concentration area 22 caused by the stress concentration, but the range of the stress concentration area 22 remains almost unchanged. For this reason, even when the stress level of the applied cyclic tensile stress F varies, the stress concentration area 22 can be avoided by forming the holes 18a in the respective areas around the tip portion 14a of the fatigue crack 14, as well as between the crack extension direction and the directions 24 at the angle θ of 55 degrees to the crack extension direction.

The press-fitting step (S12) is a step of making the compressive stress act on the tip portion 14a of the fatigue crack 14 from the directions lateral to the crack extension direction by press-fitting the press-fit objects 20, which are higher in stiffness than the metal member body 12 and are larger in external size than the holes 18, into the holes 18.

Figure 7A:
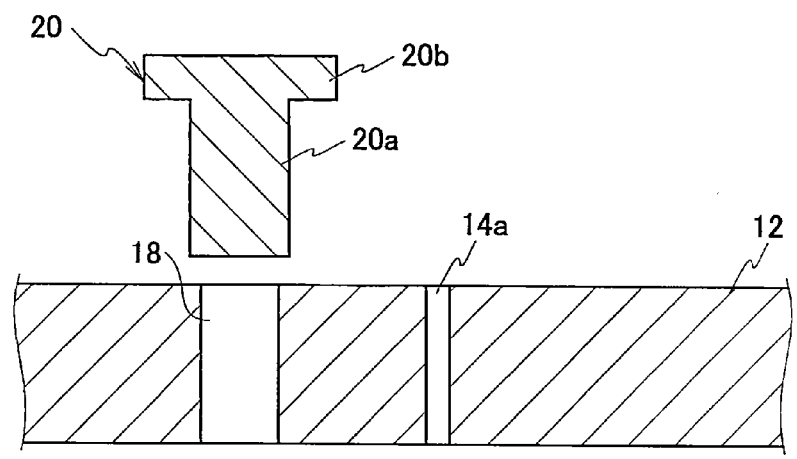
FIG. 7A is a cross-sectional view showing a state preceding the press-fitting of the press-fit object in the embodiment of the present invention.
Figure 7B:
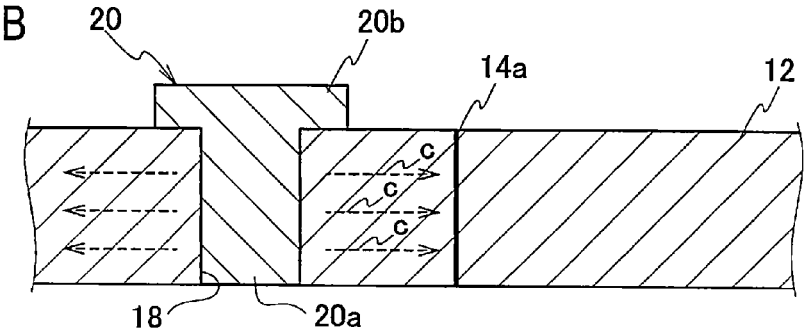
FIG. 7B is a cross-sectional view showing a state following the press-fitting of the press-fit object in the embodiment of the present invention.

FIG. 7A is a cross-sectional view showing a state preceding the press-fitting of the press-fit object 20. FIG. 7B is a cross-sectional view showing a state following the press-fitting of the press-fit object 20.

First of all, as shown in FIG. 7A, the position of the press-fit object 20 is aligned to the position of the hole 18. A pin for press-fitting, a stud or the like is used as the press-fit object 20, for example. The press-fit object 20 is press-fitted into the hole, for example by being hammered, or by use of pneumatic pressure, hydraulic pressure, explosive, or the like. As shown in FIG. 7B, once the press-fit object 20 is press-fitted, the press-fit object 20 expands the hole 18 wider, and thereby, the compressive stress C acts from the directions lateral to the crack extension direction. The opening of the tip portion 14a of the fatigue crack 14 can be pressed and closed by the compressive stress C.

The outer diameter of the press-fit portion 20a of the press-fit object 20 and the hole diameter of the hole 18 are determined on the basis of the magnitude of the compressive stress C to be made to act from the directions lateral to the crack extension direction. The outer diameter of the press-fit portion 20a is 1.1 to 1.15 times as large as the hole diameter of the hole 18, for example. When the hole diameter of the hole 18 is 4.0 mm, the outer diameter of the press-fit portion 20a is 4.5 mm.

It should be noted that in some cases later, the press-fit object 20 may be pulled out of the hole 18 for the purpose of welding repair as a permanent countermeasure against the fatigue crack 14. Since the press-fit object 20 is hard to be pulled out of the hole 18 due to friction between the metal member body 12 and the press-fit portion 20a, a flange, screw threads, a groove or the like may be provided in the head portion 20b of the press-fit object 20 for the purpose of enabling the press-fit object 20 to be easily pulled out of the hole 18 with a jig or the like.

Figure 8A:
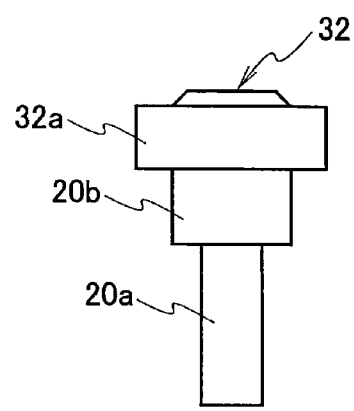
FIG. 8A is side views showing structures of press-fit objects in the embodiment of the present invention.
Figure 8B:
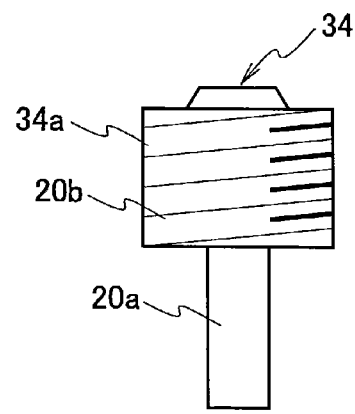
FIG. 8B is side views showing structures of press-fit objects in the embodiment of the present invention.
Figure 8C:
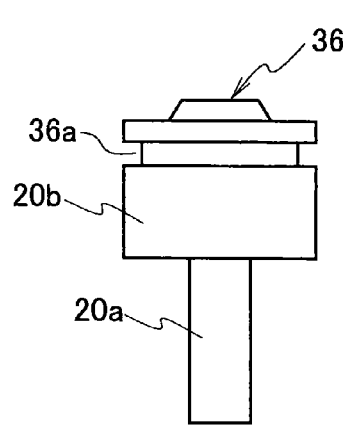
FIG. 8C is side views showing structures of press-fit objects in the embodiment of the present invention.
Figure 8D:
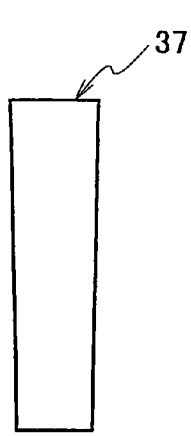
FIG. 8D is side views showing structures of press-fit objects in the embodiment of the present invention.
Figure 8E:
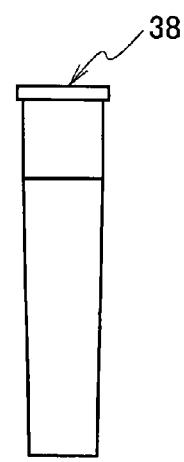
FIG. 8E is side views showing structures of press-fit objects in the embodiment of the present invention.

FIGS. 8A, 8B, 8C, 8D, and 8E depict side views showing structures of press-fit objects 32, 34, 36, 37, 38. In the press-fit object 32 shown in FIG. 8A, a flange 32a is provided on the outer peripheral surface of the head portion 20b. In the press-fit object 34 shown in FIG. 8B, screw threads 34a are provided in the outer peripheral surface of the head portion 20b. In the press-fit object 36 shown in FIG. 8C, a groove 36a is provided in the outer peripheral surface of the head portion 20b. As described above, when the outer peripheral surface of the head portion 20b is provided with any of the flange 32a, the screw threads 34a, the groove 36a or the like, the press-fit object 32, 34, or 36 can be easily pulled out of the metal member body 12 with the jig or the like. Meanwhile, the press-fit objects 37, 38 shown in FIGS. 8D and 8E are tapered. This tapering of the press-fit objects 37, 38 makes it easy to press-fit the press-fit objects 37, 38, and makes it possible to press-fit the press-fit objects 37, 38 while arresting their buckling even when the plate thickness of the metal member body 12 is thick, for example.

Figure 9A:
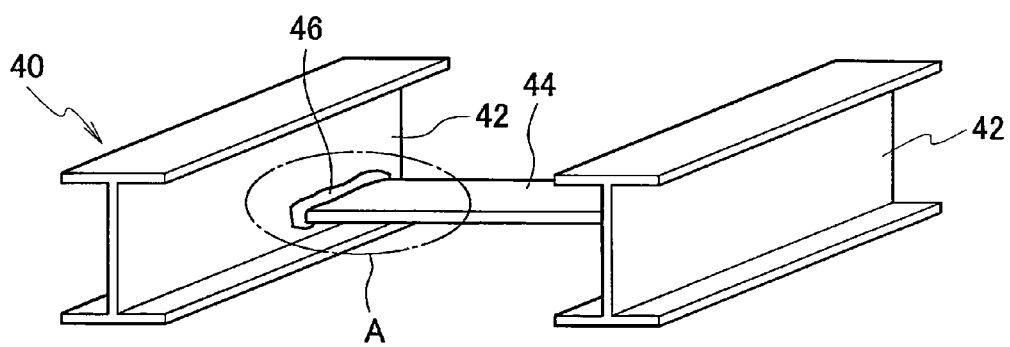
FIG. 9A is a perspective view showing the overall configuration of the metal structural body of the bridge in the embodiment of the present invention.
Figure 9B:
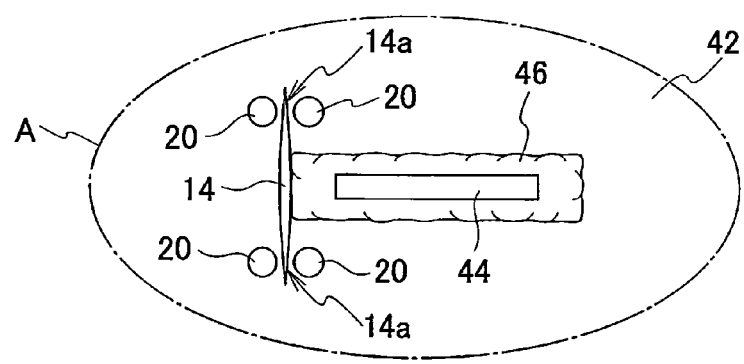
FIG. 9B is a magnified view of an area A shown in FIG. 9A in the embodiment of the present invention.

Next, descriptions will be provided for how the fatigue crack growth arresting method is applied to a metal structural body of a bridge. FIG. 9A is a perspective view showing the overall configuration of the metal structural body 40 of the bridge. FIG. 9B is a magnified view of an area A shown in FIG. 9A.

As shown in FIG. 9A, as a member typical of the metal structural body 40 of the bridge, a cross beam 44 is attached to multiple main beams 42 by boxing for the purpose of connecting the main beams 42 together. If the repeatedly applied stress is loaded on the metal structural body 40, the fatigue crack 14 may occur at a toe of weld of a welded portion 46 in some cases, as shown in FIG. 9B. The fatigue crack growth can be arrested by: forming the holes beside the tip portion 14a of the fatigue crack 14 with respect to the crack extension direction; and press-fitting the press-fit objects 20 into the respective holes. It should be noted that this method is applicable not only to the metal structural body 40 of the bridge, but also to an inner structural member of a ship, a main tower of a crane for an automated warehouse, and the like.

According to the above-described configuration, in the metal member body in which the fatigue crack occurs due of the action of the applied cyclic tensile stress, the holes are formed beside the tip portion of the fatigue crack with respect to the crack extension direction; the press-fit objects, which are higher in stiffness than the metal member body and are larger in external size than the holes, are press-fitted into the holes; and thereby, the compressive stress is made to act on the tip portion of the fatigue crack from the directions lateral to the crack extension direction. For this reason, the opening of the tip portion of the fatigue crack can be made smaller by being pressed by use of the compressive stress. Furthermore, even when the applied cyclic tensile stress acts on the metal member body, the expansion of the opening of the tip portion of the fatigue crack can be arrested since the compressive stress acts on the tip portion of the fatigue crack from the directions lateral to the crack extension direction.

According to the above-described configuration, the holes are formed beside the tip portion of the fatigue crack with respect to the crack extension direction by use of a drill or the like, and the press-fit objects are press-fitted into the holes by hitting with a hammer and the like. For this reason, the work can be easily done without large-scale equipment including a welding machine. Accordingly, whenever a fatigue crack is found during an inspection of the metal structure, the method is applicable as a temporary repair on site. Furthermore, at the time of a permanent countermeasure against the fatigue crack, it is done to pull the press-fit objects out of the holes, and to fill up the holes by welding or the like. Thus, the permanent countermeasure can also be done easily.

According to the foregoing configuration, when the length of the holes in the thickness direction of the metal member body and the length of the press-fit objects are adjusted, it is possible to arrest not only the growth of the fatigue crack which occurs in the surface portion of the metal member body, but also the growth of the fatigue crack penetrating the metal member body in its thickness direction.

EXAMPLES

Next, the effectiveness of the fatigue crack growth arresting method was evaluated by conducting fatigue tests.
(Specimen for Fatigue Test)

Figure 10:
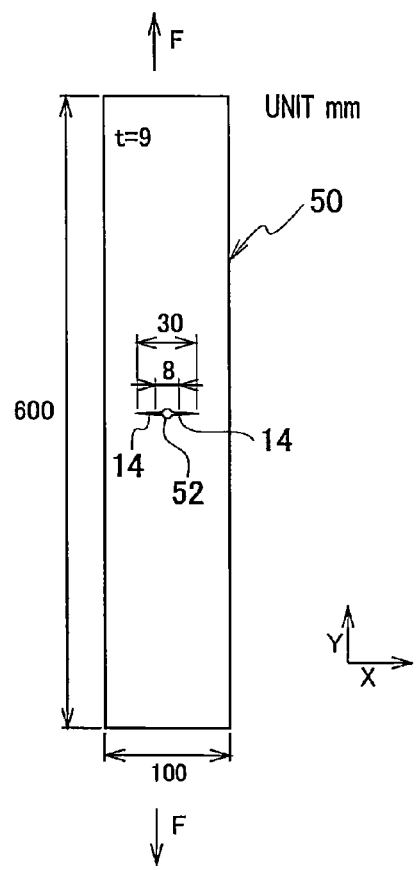
FIG. 10 is a plan view showing a shape of a specimen for fatigue test in the embodiment of the present invention.

FIG. 10 is a plan view showing the shape of a specimen for fatigue test 50. The specimen for fatigue test 50 was shaped like a flat rectangular plate, which was 600 mm in length, 100 mm in width and 9 mm in plate thickness. Mild steel (JIS SS400, SM490 and the like) was used for the specimen for fatigue test 50. A hole 52 with a diameter of 4 mm was made in the center of the specimen for fatigue test 50 by use of a drill, and slits were formed on two sides of the hole 52 (in the directions orthogonal to the longitudinal direction of the specimen for fatigue test 50) by electro-discharge machining. The length of each slit from the center of the hole 52 was set at 4 mm. The length from a tip of one slit to a tip of the other slit was set at 8 mm. Furthermore, the width of each slight was set at 0.2 mm.

Figure 11:
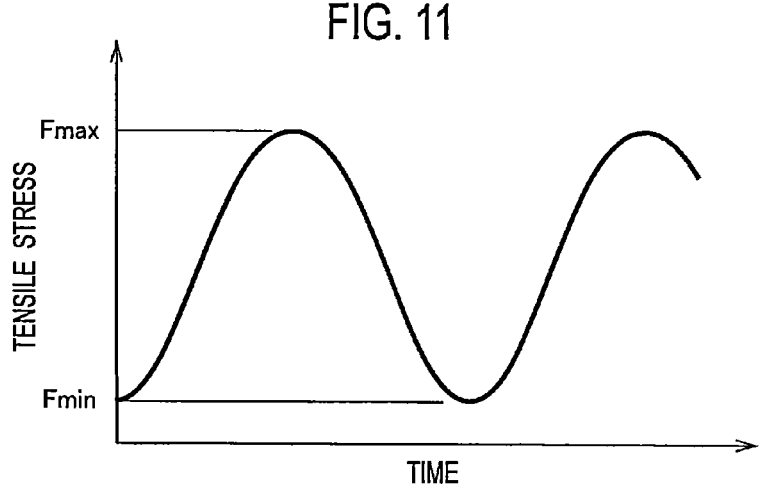
FIG. 11 is a graph showing applied cyclic tensile stress which was made to act on the specimen for fatigue test.

Subsequently, the fatigue cracks 14 were introduced into the specimen for fatigue test 50 by making the applied cyclic tensile stress F act on the specimen for fatigue test 50. FIG. 11 is a graph showing the applied cyclic tensile stress F which was made to act on the specimen for fatigue test 50. The applied cyclic tensile stress F was made to act thereon in the longitudinal direction of the specimen for fatigue test 50. The maximum tensile stress (nominal stress) Fmax of the applied cyclic tensile stress F was set at 90 MPa, and the minimum tensile stress Fmin thereof was set at 0 MPa. The reason why the maximum tensile stress of the applied cyclic tensile stress F was set at 90 MPa is that when a fatigue crack occurs in a metal structural body of a bridge, the maximum value of applied cyclic tensile stress acting on the metal structural body is in a range of 70 MPa to 80 MPa. In addition, the frequency of the applied cyclic tensile stress F to be made to act on the specimen for fatigue test 50 was set at 5 Hz.

A fatigue testing machine was used to make the applied cyclic tensile stress F to act on the specimen for fatigue test 50 in which the slits were made. Thus, the fatigue cracks 14 were introduced into the specimen for fatigue test 50 by letting the fatigue cracks 14 grow as long as 15 mm each from the center of the hole 52 (as long as 30 mm from the tip of the one fatigue crack 14 to the tip of the other fatigue crack 14).
(Examination on Locations of Holes)

Examination was made on the locations of the holes in the specimen for fatigue test 50 for arresting the fatigue crack growth. First of all, the stress analysis using the finite element method (FEM) was performed on the distribution of stress which occurred around the tip portion 14a of the fatigue crack 14 when tensile stress was made to act uniformly on the specimen for fatigue test 50 in its longitudinal direction.

Figure 12:
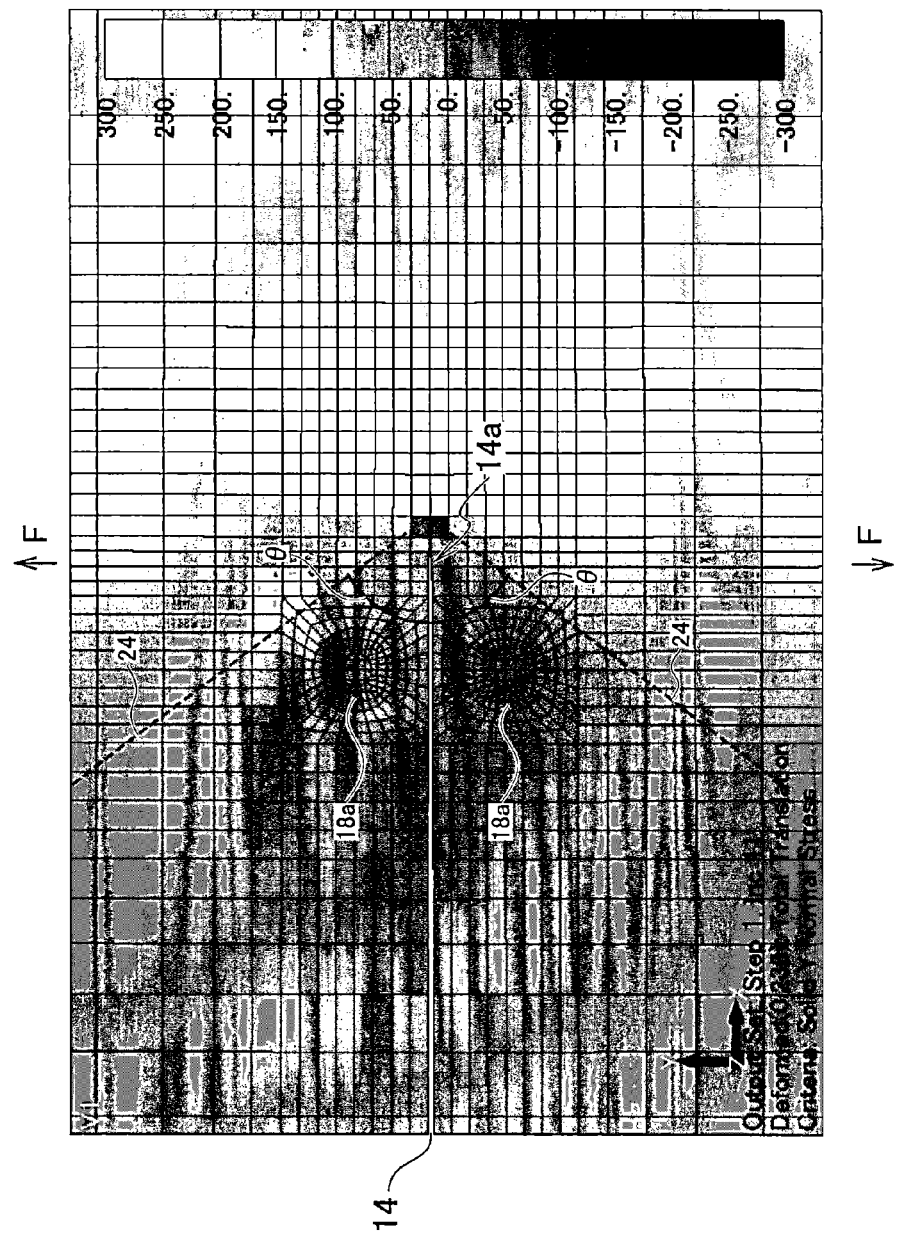
FIG. 12 is a diagram showing distribution of stress in a longitudinal direction of the specimen for fatigue test which occurred around the tip portion of the fatigue crack in the embodiment of the present invention.

FIG. 12 is a diagram showing the distribution of stress in the longitudinal direction of the specimen for fatigue test 50 which occurred around the tip portion 14a of the fatigue crack 14. The maximum tensile stress (nominal stress) of the applied cyclic tensile stress F at 90 MPa was made to act uniformly on the specimen for fatigue test 50 in its longitudinal direction. A grayscale represents the level of stress around the tip portion 14a of the fatigue crack 14, and indicates that: the tensile stress is larger in a region where white is emphasized more; and the compressive stress is larger in a region where black is emphasized more.

As clear from FIG. 12, it was confirmed that the stress concentration on the tip of the fatigue crack 14 caused a stress concentration area where the tensile stress was larger than the tensile stress at 90 MPa made to act uniformly on the specimen for fatigue test 50. In addition, it was confirmed that circumvention of the tip of the fatigue crack 14 by the lines of stress of the tensile stress caused stress areas, where the tensile stress was smaller than the tensile stress at 90 MPa made to act uniformly on the specimen for fatigue test 50, around the tip portion 14a of the fatigue crack 14.

With these taken into consideration, in the following fatigue test, it was determined that the holes 18a be provided in locations outside the stress concentration area which was caused by the stress concentration. From the stress analysis shown in FIG. 12, it was given that part or all of each hole 18a could be prevented from being included in the stress concentration area, where the tensile stress caused by the stress concentration was greater, by forming the holes 18a in their respective areas around the tip portion 14a of the fatigue crack 14, as well as between the crack extension direction and the directions at the angle θ of 55 degrees to the crack extension direction.

(Examination on Distribution of Stress by Press-Fitting)

Figure 13B:
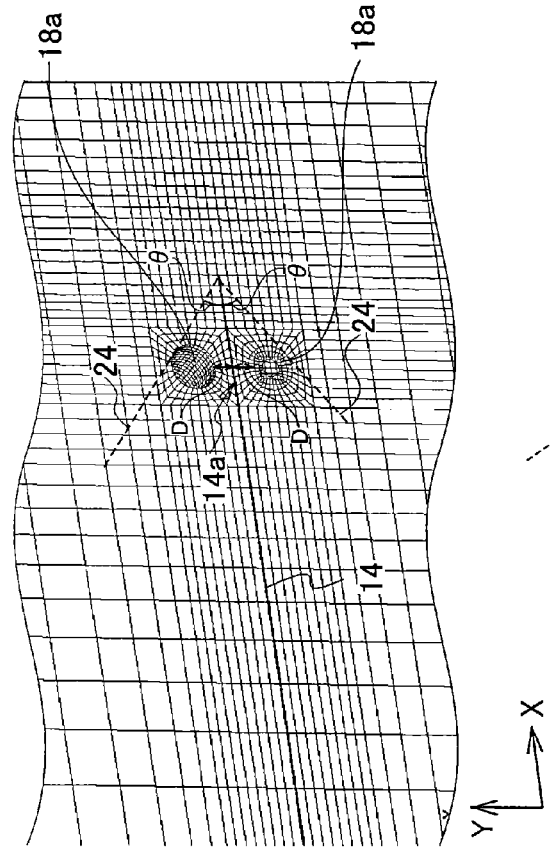
FIG. 13B is a magnified diagram of the model showing an area A shown in FIG. 13A in the embodiment of the present invention.
Figure 13C:
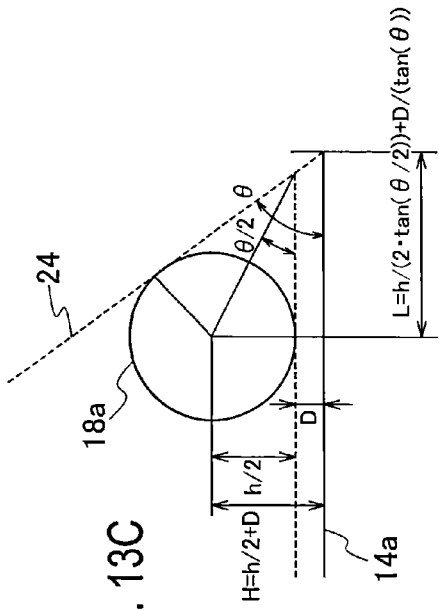
FIG. 13C is a magnified diagram of the model showing the vicinity of one of the holes shown in FIG. 13B in the embodiment of the present invention.
Figure 13A:
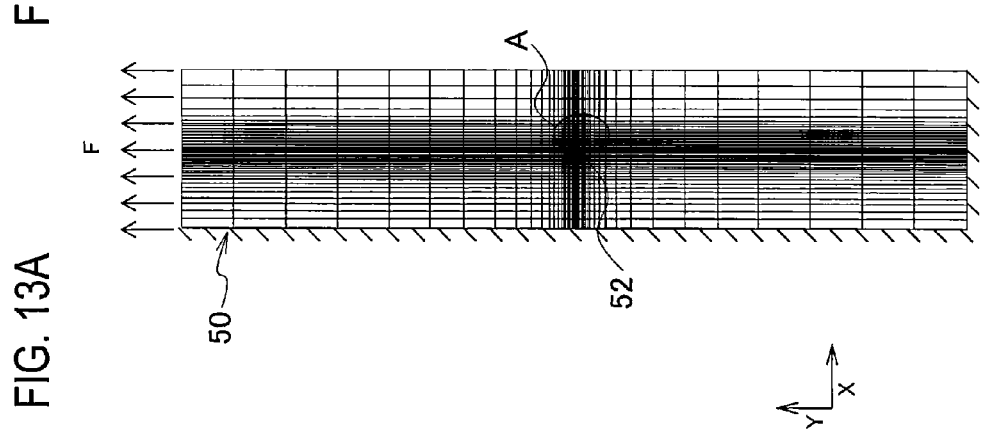
FIG. 13A is a diagram of the model for the specimen for fatigue test used for the stress analysis in the embodiment of the present invention.

Thereafter, another stress analysis using the finite element method (FEM) was performed on influences to the tip portion 14a of the fatigue crack 14 when the press-fit objects 20 were press-fitted into the holes 18a. FIG. 13A is a diagram of the model for the specimen for fatigue test 50 used for the stress analysis. FIG. 13B is a magnified diagram of the model showing an area A shown in FIG. 13A. FIG. 13C is a magnified diagram of the model showing the vicinity of one of the holes 18a shown in FIG. 13B.

The holes 18a were round holes each with a hole diameter (h) of 4 mm. The two holes 18a were placed in locations symmetrical, in the direction orthogonal to the crack extension direction, with respect to the tip portion 14a of each of the fatigue cracks 14 introduced into the two sides of the hole 52. Furthermore, for the purpose of providing the holes 18a in the locations outside the stress concentration area caused by the stress concentration on the tip of the fatigue crack 14, the holes 18a were placed in the locations around the tip portion 14a of the fatigue crack 14 and between the crack extension direction and directions 24 at the angle θ of 55 degrees to the crack extension direction. Moreover, for the purpose of preventing the peripheral edge of each hole 18a and the tip portion 14a of the fatigue crack 14 from connecting with each other at the time of the press-fitting, the hole 18a was placed in the location where the shortest distance D between the peripheral edge of the hole 18a and the tip portion 14a of the fatigue crack 14 was 1 mm. The length H of the perpendicular line to the tip portion 14a of the fatigue crack 14 from the center of the hole 18a was 3.0 mm. The distance L between the tip of the fatigue crack 14 and the foot of the perpendicular line to the tip portion 14a of the fatigue crack 14 from the center of the hole 18 was 4.5 mm.

The stress analysis using the finite element method (FEM) was performed on the assumption that a stud for press-fitting with an outer diameter of 4.5 mm was used as each press-fit object 20, and by simulating the press-fitting to expand the hole 18a from its original hole diameter of 4 mm to a hole diameter of 4.5 mm by forced displacement. Furthermore, the stress analysis was performed under conditions that: the lower end portion of the specimen for fatigue test 50 was restrained in its longitudinal direction; symmetry was established with respect to directions orthogonal to the longitudinal direction of the specimen for fatigue test 50; and the surfaces of the fatigue crack were brought into contact (contact analysis).

Figure 14:
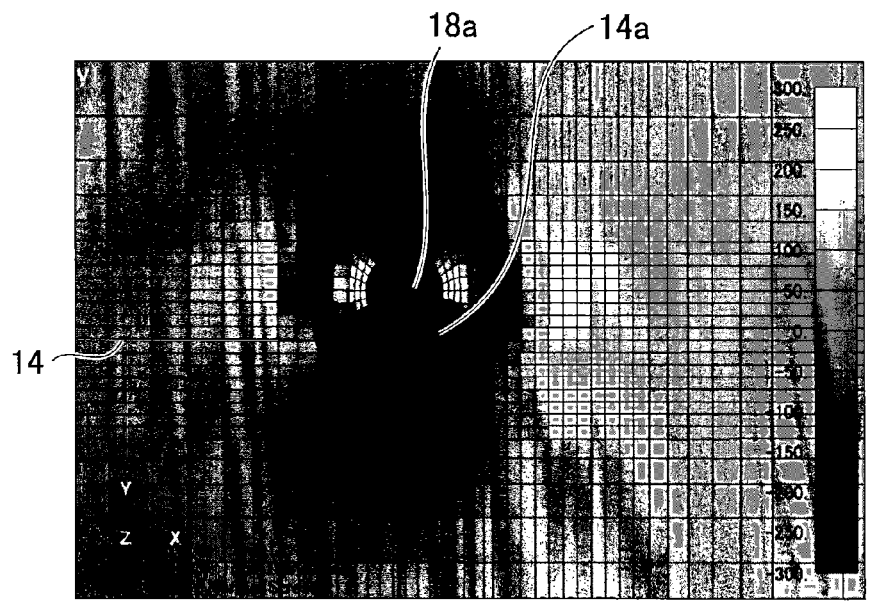
FIG. 14 is a diagram showing distribution of stress in the longitudinal direction of the specimen for fatigue test in association with press-fitting of a press-fit object into the specimen for fatigue test in the embodiment of the present invention.

FIG. 14 is a diagram showing distribution of stress in the longitudinal direction of the specimen for fatigue test 50 associated with the press-fitting of the press-fit object 20. A grayscale represents the level of stress acting on the vicinity of the tip portion 14a of the fatigue crack 14. Like FIG. 12, FIG. 14 indicates that: the tensile stress is larger in a region where white is emphasized more; and the compressive stress is larger in a region where black is emphasized more. It was confirmed that: the compressive stress acted on the tip portion 14a of the fatigue crack 14 from the directions lateral to the crack extension direction; and the opening of the tip portion 14a of the fatigue crack 14 was pressed.

Figure 15:
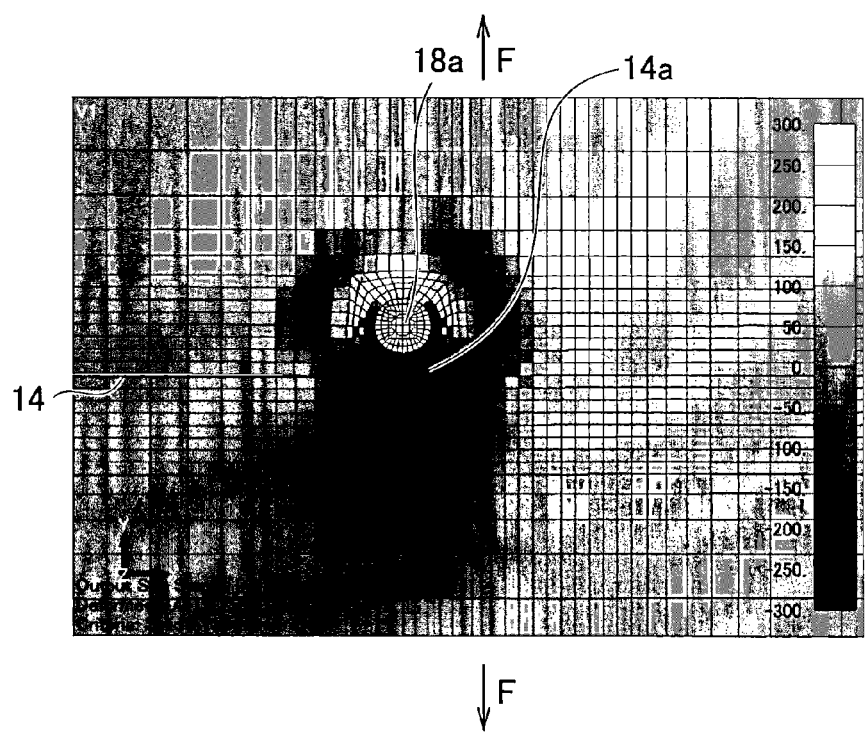
FIG. 15 is a diagram showing distribution of stress in the longitudinal direction of the specimen for fatigue test when uniform tensile stress was made to act on the specimen for fatigue test after the press-fitting in the embodiment of the present invention.

Yet another stress analysis using the finite element method (FEM) was performed on the distribution of stress which occurred when uniform tensile stress was made to act on the specimen for fatigue test 50 in its longitudinal direction. FIG. 15 is a diagram showing the distribution of stress in the longitudinal direction of the specimen for fatigue test 50 which occurred when the uniform tensile stress was made to act on the specimen for fatigue test 50 after the press-fitting. The tensile stress made to act uniformly on the specimen for fatigue test 50 in its longitudinal direction was set at 90 MPa as nominal stress. The grayscale represents the level of stress acting around the tip portion 14a of the fatigue crack 14. Like in FIG. 12, the grayscale indicates that: the tensile stress is larger in a region where white is emphasized more; and the compressive stress is larger in a region where black is emphasized more.

It was confirmed that: even when the uniform tensile stress was made to act on the specimen for fatigue test 50, the compressive stress acting from the directions lateral to the crack extension direction remained on the tip portion 14a of the fatigue crack 14; and the opening of the tip portion 14a of the fatigue crack 14 remained pressed and closed.

(Fatigue Crack Growth Arresting Process)

On the basis of the results of the stress analyses, the holes 18a each with the hole diameter of 4 mm were formed by being drilled in the specimen for fatigue test 50, into which the fatigue cracks 14 were introduced. As shown in the model in FIGS. 13A, 13B and 13C, the locations of the holes 18a were situated around the tip portion 14a of the fatigue crack 14 and between the crack extension direction and the directions 24 at the angle θ of 55 degrees to the crack extension direction, and made the shortest distance D between the peripheral edge of each hole 18a and the tip portion 14a of the fatigue crack 14 equal to 1 mm. Furthermore, the length H of the perpendicular line to the tip portion 14a of the fatigue crack 14 from the center of the hole 18a was set at 3.0 mm. The distance L between the tip of the fatigue crack 14 and the foot of the perpendicular line to the tip portion 14a of the fatigue crack 14 from the center of the hole 18a was set at 4.5 mm.

The four holes 18a in total were formed by: providing two holes 18a on the two sides to the crack extension direction of the tip portion 14a of the fatigue crack 14 on one side of the hole 52; and providing the other two holes 18a on the two sides to the crack extension direction of the tip portion 14a of the fatigue crack 14 on the other side of the hole 52. The two holes 18a provided on the two sides to the crack extension direction of the tip portion 14a of each fatigue crack 14 were placed symmetrical with respect the tip portion 14a of the fatigue crack 14 in the direction orthogonal to the crack extension direction (the direction in parallel with the direction of the applied cyclic tensile stress).

Figure 16:
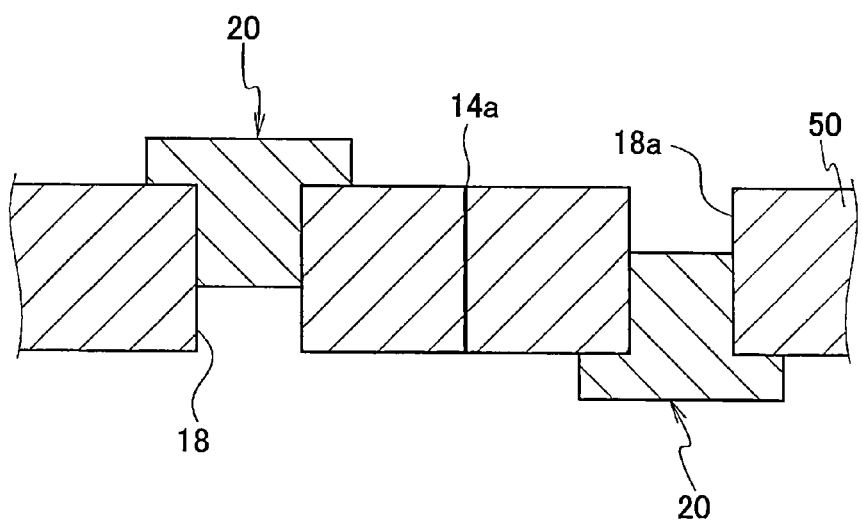
FIG. 16 is a cross-sectional view showing an area around a tip portion of one of fatigue cracks after driving in of studs in the embodiment of the present invention.

Studs (X-BT M8-15-6 SN12-R) manufactured by Hilti Corporation, which were higher in stiffness than mild steel, were used as the press-fit objects 20. The studs of this type were made from CR500 (austenite stainless steel). The press-fit portion of each stud was 4.5 mm in outer diameter, and 5 mm in length. The studs were hammered into the four holes 18a formed in the specimen for fatigue test 50 including the introduced fatigue cracks 14. FIG. 16 is a cross-sectional view showing the vicinity of the tip portion 14a of one of the fatigue cracks 14 after the studs were hammered in. As shown in FIG. 16, one of the studs was hammered in from one surface of the specimen for fatigue test 50, while the other of the studs was hammered in from the other surface of the specimen for fatigue test 50.

(Fatigue Test)

A fatigue test was performed on the specimen for fatigue test subjected to the foregoing fatigue crack growth arresting process. As shown in FIG. 11, as conditions for the fatigue test, the maximum tensile stress (nominal stress) was set at 90 MPa, and the minimum tensile stress was set at 0 MPa. The frequency for the fatigue test was set at 5 Hz. In addition, as a comparative example, another fatigue test was similarly performed on a specimen for fatigue test which was provided with only slits but not subjected to the foregoing fatigue crack growth arresting process.

Figure 17:
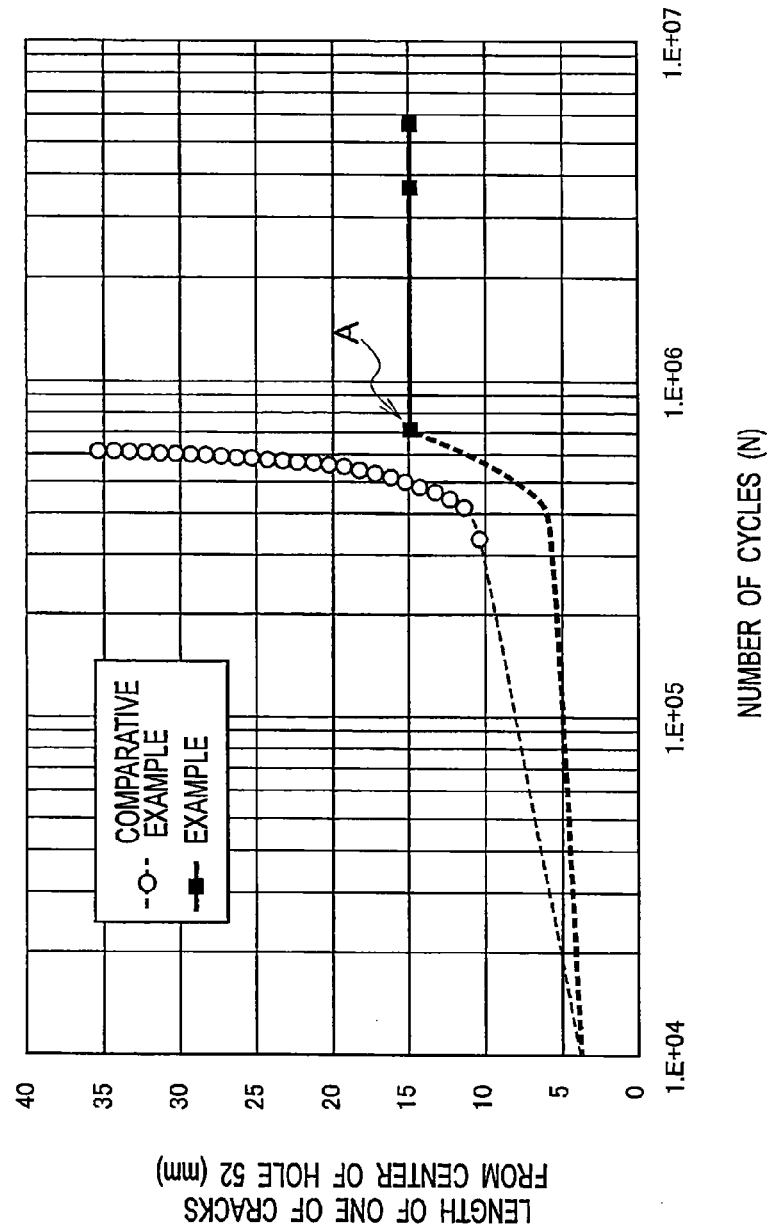
FIG. 17 is a graph showing results of fatigue tests in the embodiment of the present invention.

FIG. 17 is a graph showing the results of the fatigue tests. In the graph shown in FIG. 17, the horizontal axis represents the number (N) of cycles; the vertical axis represents the length (mm) of one of the fatigue cracks from the center of the hole 52; data on the example subjected to the fatigue crack growth arresting process is plotted with black squares; and data on the comparative example is plotted with white circles.

It should be noted that, as described above, the fatigue test was performed on the specimen for fatigue test of the example by: causing the one of the fatigue cracks to grow up to a length (mm) of 15 mm from the center of the hole 52 (corresponding to Point of Time A in FIG. 17 when the number of cycles stood at approximately 700 thousand) in advance; then detaching the specimen for fatigue test from the fatigue testing machine, and subjecting the specimen for fatigue test to the foregoing fatigue crack growth arresting process; and again attaching the resultant specimen for fatigue test to the fatigue testing machine, and resuming the fatigue test.

In the specimen for fatigue test of the comparative example, the length of one of the fatigue cracks from the center of the hole 52 exceeded 35 mm when the number of cycles reached approximately 620 thousand, and was eventually broken. In contrast to this, in the specimen for fatigue test of the example, the length of the one fatigue crack from the center of the hole 52 remained almost unchanged from before the fatigue crack growth arresting process, even after the number of cycles after the fatigue crack growth arresting process exceeded 6 million. The results of the fatigue tests made it clear that the fatigue crack growth was arrested in the specimen for fatigue test of the example compared to the specimen for fatigue test of the comparative example.

Thereafter, the effectiveness of the fatigue crack growth arresting process was further evaluated by: changing the locations of the holes into which to press-fit the studs as the press-fit objects; and changing the stress level of the applied cyclic tensile stress F. At the same time, the fatigue crack growth arresting method using the so-called stop-holes was evaluated.

First of all, descriptions will be provided for fatigue crack growth arresting processes of Examples A, B. For the fatigue crack growth arresting processes of Examples A, B, specimens for fatigue test were used which had the same shape as the specimen for fatigue test 50 including the introduced fatigue cracks, shown in FIG. 10, used for the fatigue crack growth arresting process of the foregoing example (the rectangular specimen which was 100 mm in width, 600 mm in length and 9 mm in thickness), and which were made from the same material (mild steel; JIS SS400, SM 490 or the like) as the specimen for fatigue test 50.

In addition, the fatigue cracks were introduced by using the same fatigue crack introducing method as used for producing the specimen for fatigue test 50 to be used in the fatigue crack growth arresting process of the foregoing example, except that: the maximum tensile stress (nominal stress) Fmax of the applied cyclic tensile stress F for the introduction of the fatigue cracks was set at 120 MPa; and the minimum tensile stress Fmin thereof was set at 0 MPa.

In other words, as in the case of the specimen for fatigue test 50 shown in FIG. 10, slits were introduced into each specimen for fatigue test by electro-discharge machining (with the length of each slit from the center of the hole 52 set at 4 mm, and with the length from a tip of one slit to a tip of the other slit set at 8 mm). Thereafter, the fatigue testing machine made the applied cyclic tensile stress F act on the resultant specimen for fatigue test, and thereby, each of the fatigue cracks 14 was caused to grow to the length of 15 mm from the center of the hole 52 (with the length from the tip of the one fatigue crack 14 to the tip of the other fatigue crack 14 reaching 30 mm).

Figure 18:
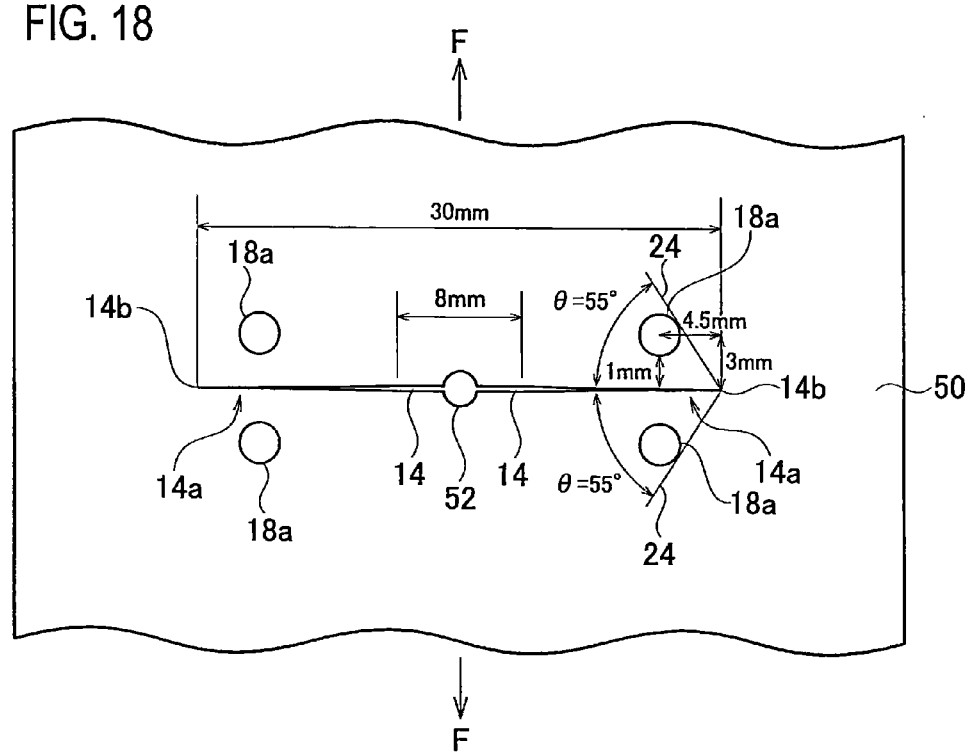
FIG. 18 is a magnified view of an area in a specimen for fatigue test including introduced fatigue cracks, where holes into which to press-fit studs as press-fit objects were formed for a fatigue crack growth arresting process of Example A in the embodiment of the present invention.

The fatigue crack growth arresting process of Example A was performed in the same manner as the fatigue crack growth arresting process of the foregoing example. FIG. 18 is a magnified view of an area in the specimen for fatigue test 50 including the introduced fatigue cracks 14, where the holes 18a into which to press-fit the studs as the press-fit objects were formed for the fatigue crack growth arresting process of Example A.

The holes 18a each with the hole diameter of 4 mm were formed, by being drilled, in the specimen for fatigue test 50 including the introduced fatigue cracks 14. As shown in the diagram of the model in FIGS. 13A, 13B and 13C, the locations of the holes 18a were situated around the tip portion 14a of each fatigue crack 14 and between the crack extension direction of the fatigue crack 14 and the directions 24 at the angle θ of 55 degrees to the crack extension direction of the fatigue crack 14 (where the line of each of the directions 24 at the angle θ of 55 degrees to the crack extension direction of the fatigue crack 14 comes into contact with the peripheral edge of each hole 18a), and made the shortest distance between the peripheral edge of each hole 18a and the tip portion 14a of the fatigue crack 14 equal to 1 mm.

Furthermore, the length of the perpendicular line to the tip portion 14a of the fatigue crack 14 from the center of the hole 18a was set at 3 mm. The distance between the tip 14b of the fatigue crack 14 and the foot of the perpendicular line to the tip portion 14a of the fatigue crack 14 from the center of the hole 18a was set at 4.5 mm.

Furthermore, the four holes 18a in total were formed by: providing two holes 18a on the two sides to the crack extension direction of the tip portion 14a of the fatigue crack on one side of the hole 52; and providing the other two holes 18a on the two sides to the crack extension direction of the tip portion 14a of the fatigue crack on the other side of the hole 52. The two holes 18a provided on the two sides to the crack extension direction of the tip portion 14a of each fatigue crack were placed symmetrical with respect to the tip portion 14a of the fatigue crack in the direction orthogonal to the crack extension direction (the direction in parallel with the direction of the applied cyclic tensile stress F).

Thereafter, the studs (X-BT M8-15-6 SN12-R) manufactured by Hilti Corporation, whose press-fit portion was 4.5 mm in outer diameter, were hammered into the four holes 18a in the same manner as used for the fatigue crack growth arresting process of the foregoing example. Here, one specimen for fatigue test subjected to the fatigue crack growth arresting process of Example A was produced.

Figure 19:
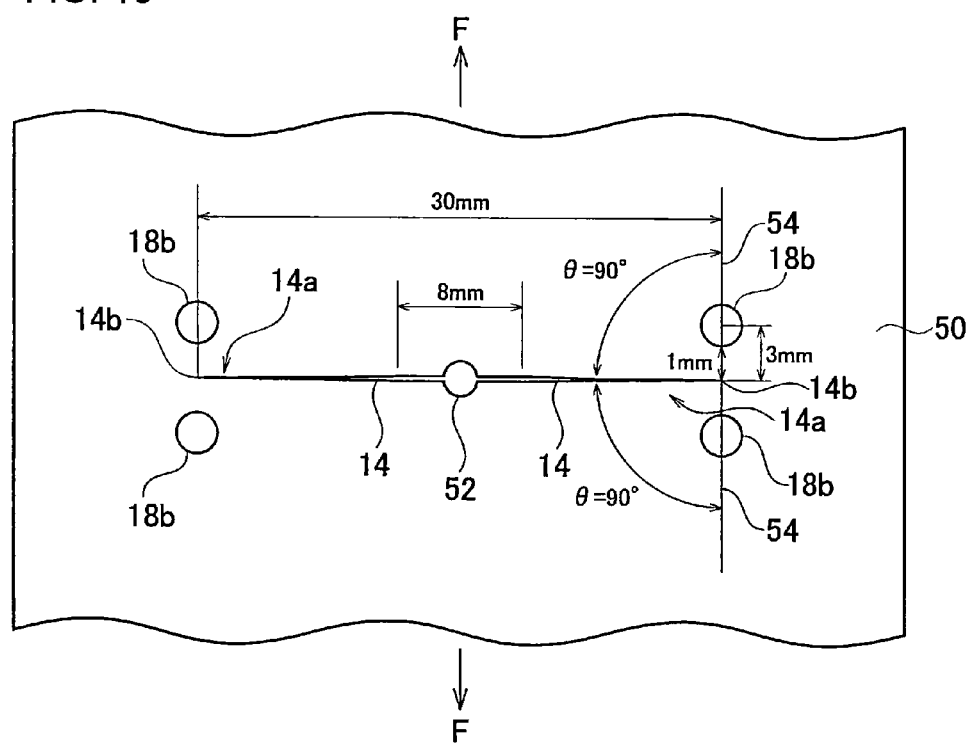
FIG. 19 is a magnified view of an area in a specimen for fatigue test including introduced fatigue cracks, where holes into which to press-fit the studs as press-fit objects were formed for a fatigue crack growth arresting process of Example B in the embodiment of the present invention.

In the fatigue crack growth arresting process of Example B, each hole into which to press-fit the stud as the press-fit object was formed in a way that a straight line joining the center of the hole and the tip of the corresponding fatigue crack was orthogonal to the crack extension direction of the fatigue crack. FIG. 19 is a magnified view of an area in the specimen for fatigue test 50 including the introduced fatigue cracks 14, where the holes 18b into which to press-fit the studs as the press-fit objects were formed for the fatigue crack growth arresting process of Example B.

The holes 18b each with the hole diameter of 4 mm were formed, by being drilled, in each specimen for fatigue test 50 including the introduced fatigue cracks 14. In the fatigue crack growth arresting process of Example B, each hole 18b into which to press-fit the stud as the press-fit object was formed in a way that a straight line 54 joining the center of the hole 18b and the tip 14b of the corresponding fatigue crack was orthogonal to the crack extension direction of the fatigue crack 14. In other words, the center of the hole 18b was situated on a straight line extending in a direction 54 orthogonal to the crack extension direction of the fatigue crack at the tip 14b. The shortest distance between the peripheral edge of the hole 18b and the tip 14b of the fatigue crack was set at 1 mm. The length of the perpendicular line to the tip 14b of the fatigue crack from the center of the hole 18b was set at 3 mm.

The four holes 18b in total were formed by: providing two holes 18b on the two sides to the crack extension direction of the tip 14b of the fatigue crack 14 on one side of the hole 52; and providing the other two holes 18b on the two sides to the crack extension direction of the tip 14b of the fatigue crack 14 on the other side of the hole 52. The two holes 18b provided on the two sides to the crack extension direction of each fatigue crack 14 at the tip 14b were placed orthogonally symmetrical with respect to the crack extension direction of the fatigue crack 14 at the tip 14b (the direction in parallel with the direction of the applied cyclic tensile stress F).

Thereafter, the studs (X-BT M8-15-6 SN12-R) manufactured by Hilti Corporation, whose press-fit portion was 4.5 mm in outer diameter, were hammered into the four holes 18b in the same manner as used for the fatigue crack growth arresting process of the foregoing example. Here, two specimens for fatigue test subjected to the fatigue crack growth arresting process of Example B were produced.

As Comparative Example A, a fatigue crack growth arresting method using the so-called stop-holes was evaluated as well.

For the fatigue crack growth arresting process of Comparative Example A, specimens for fatigue test were used which had the same shape as the specimen for fatigue test 50 including the introduced fatigue cracks, shown in FIG. 10, used for the fatigue crack growth arresting process of the foregoing example (the rectangular specimen which was 100 mm in width, 600 mm in length and 9 mm in thickness), and which were made from the same material (mild steel; JIS SS400, SM 490 or the like) as the specimen for fatigue test 50.

In addition, the fatigue cracks were introduced by using the same fatigue crack introducing method as used for producing the specimen for fatigue test 50 used in the fatigue crack growth arresting process of the foregoing example. In other words, as in the case of the specimen for fatigue test 50 shown in FIG. 10, slits were introduced into each specimen for fatigue test by electro-discharge machining (with the length of each slit from the center of the hole 52 set at 4 mm, and with the length from a tip of one slit to a tip of the other slit set at 8 mm). Thereafter, the fatigue testing machine made the applied cyclic tensile stress F act on the resultant specimen for fatigue test, and thereby, each of the fatigue cracks 14 was caused to grow to the length of 15 mm from the center of the hole 52 (with the length from the tip of the one fatigue crack 14 to the tip of the other fatigue crack 14 reaching 30 mm).

In this respect, one of the specimens for fatigue test was produced by: setting the maximum tensile stress (nominal stress) Fmax of the applied cyclic tensile force F for the introduction of the fatigue cracks at 90 MPa; and the minimum tensile stress Fmin thereof at 0 MPa. The other of the specimens for fatigue test was produced by: setting the maximum tensile stress (nominal stress) Fmax thereof at 120 MPa; and the minimum tensile stress Fmin thereof at 0 MPa.

Figure 20:
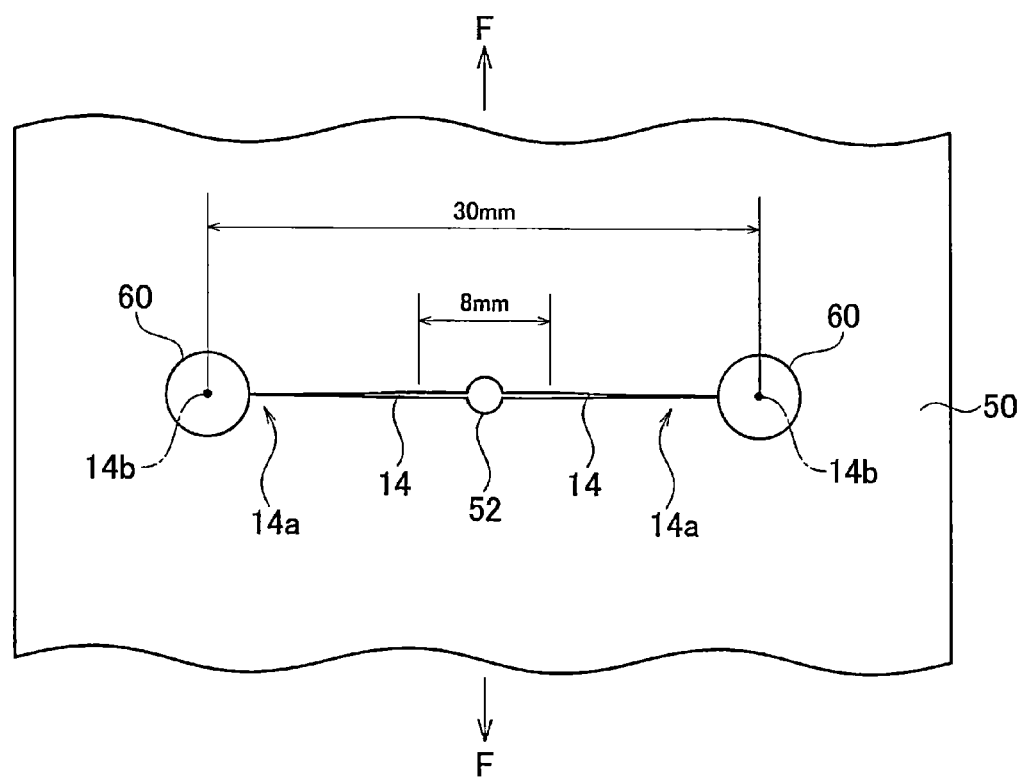
FIG. 20 is a magnified view of an area in a specimen for fatigue test including introduced fatigue cracks, where stop holes were formed for a fatigue crack growth arresting process of Comparative Example A.

Thereafter, the stop-holes were formed in each specimen for fatigue test including the introduced fatigue cracks. FIG. 20 is a magnified view of an area in the specimen for fatigue test 50 including the introduced fatigue cracks 14, where stop holes 60 were formed for the fatigue crack growth arresting process of Comparative Example A.

The two stop-holes 60 in total were formed, by being drilled, respectively around a tip 14b of one fatigue crack on one side of the hole 52 and a tip 14b of the other fatigue crack on the other side of the hole 52. The hole diameter of each stop-hole 60 was set at 18 mm.

A fatigue test was performed in atmosphere at room temperature on the specimens for fatigue test subjected to the fatigue crack growth arresting processes of Examples A, B and Comparative Example A. As fatigue test conditions for the specimens for fatigue test subjected to the fatigue crack growth arresting processes of Examples A, B, the maximum tensile stress (nominal stress) Fmax was set at 120 MPa, and the minimum tensile stress Fmin was set at 0 MPa. The frequency of the fatigue test was set at 5 Hz. In addition, the length of each fatigue crack was measured with a crack gauge. Here, the one specimen for fatigue test subjected to the fatigue crack growth arresting process of Example A was tested, while the two specimens for fatigue test subjected to the fatigue crack growth arresting process of Example B were tested.

The two specimens for fatigue test subjected to the fatigue crack growth arresting process of Comparative Example A were tested. As fatigue test conditions for one of the specimens for fatigue test, the maximum tensile stress (nominal stress) Fmax was set at 90 MPa, and the minimum tensile stress Fmin was set at 0 MPa. As fatigue test conditions for the other of the specimens for fatigue test, the maximum tensile stress (nominal stress) was set at 120 MPa, and the minimum tensile stress Fmin was set at 0 MPa. Furthermore, the frequency of the fatigue test was set at 5 Hz. It should be noted that for the specimens for fatigue test subjected to the fatigue crack growth arresting process of Comparative Example A, the lengths of their fatigue cracks were not measured with the crack gauge since the stop-holes were formed at the extremities of the fatigue cracks.

Figure 21:
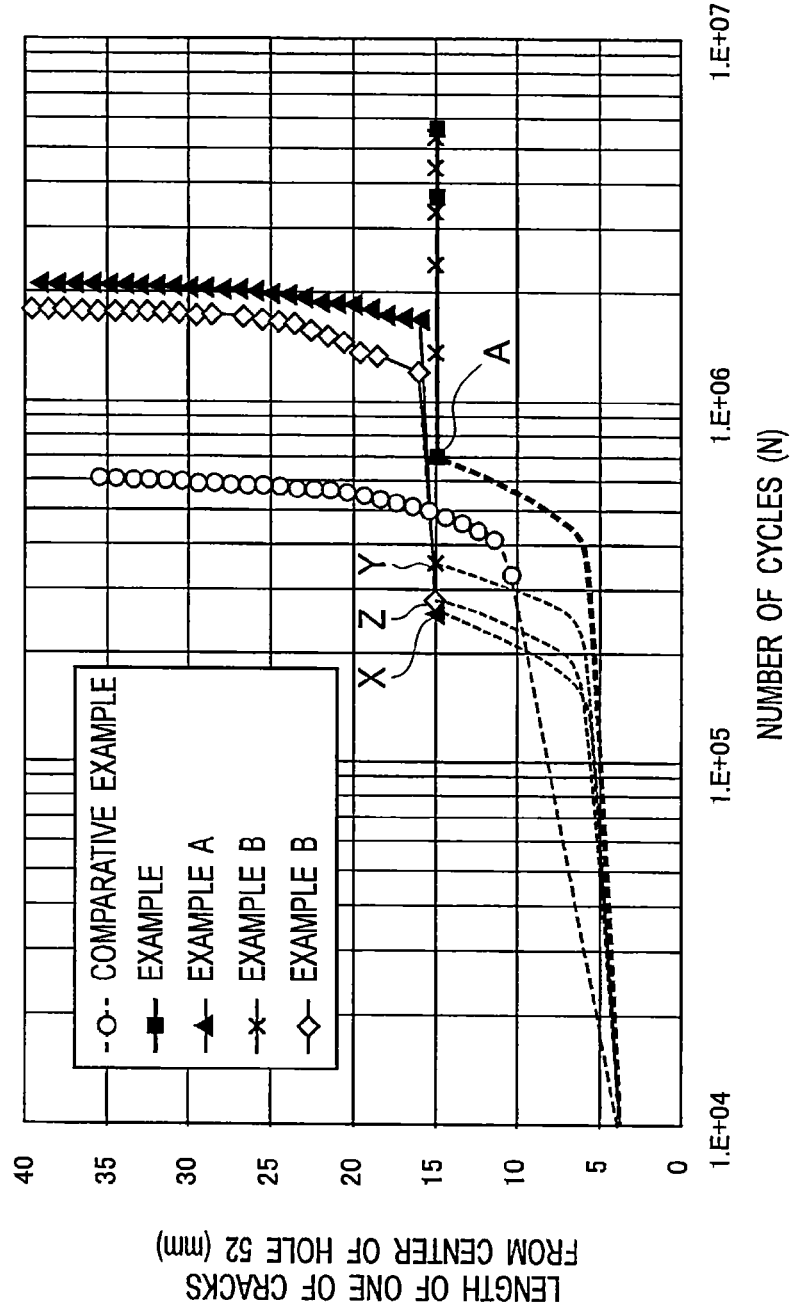
FIG. 21 is a graph showing results of fatigue tests in the embodiment of the present invention.

FIG. 21 is a graph showing results of the fatigue tests. In the graph in FIG. 21, the horizontal axis represents the number (N) of cycles, and the vertical axis represents the length (mm) of one of the fatigue cracks from the center of the hole 52. Data on the specimens for fatigue test subjected to the fatigue crack growth arresting processes of Examples A, B are plotted thereon. Here, the data on the specimen for fatigue test subjected to the fatigue crack growth arresting process of Example A are indicated with black triangles. The data on the specimens for fatigue test subjected to the fatigue crack growth arresting process of Example B are indicated with cross marks and white diamond marks.

In addition, the graph in FIG. 21 incorporates: the data on the specimen for fatigue test of the comparative example subjected to no fatigue crack growth arresting process, which are shown in FIG. 17 mentioned above (the white circles in the graph shown FIG. 17); and the data on the specimen for fatigue test subjected to the fatigue crack growth arresting process of the example, which are shown in FIG. 17 (the black squares in the graph shown in FIG. 17). The data on the specimen for fatigue test of the comparative example subjected to no fatigue crack growth arresting process are indicated with white circles, and the data on the specimen for fatigue test subjected to the fatigue crack growth arresting process of the example are indicated with black squares.

The graph in FIG. 21 further incorporates the data on the specimens for fatigue test in the course of the fatigue crack introduction preceding their respective fatigue crack growth arresting processes. As described above, in each of the specimens for fatigue test subjected to the fatigue crack growth arresting processes of Examples A, B, the length (mm) of one of the fatigue cracks from the center of the hole 52 was caused to grow to 15 mm in advance. After that time (in the graph in FIG. 21, a point X of time when the number of cycles reached approximately 260 thousand for the specimen for fatigue test subjected to the fatigue crack growth arresting process of Example A; a point Y of time when the number of cycles reached approximately 350 thousand for one of the specimens for fatigue test subjected to the fatigue crack growth arresting process of Example B; and a point Z of time when the number of cycles reached 280 thousand for the other of the specimens for fatigue test subjected thereto), the specimens for fatigue test were detached from the fatigue testing machine, and were subjected to their respective fatigue crack growth arresting processes. Thereafter, the specimens for fatigue test subjected to their fatigue crack growth arresting processes were attached to the fatigue testing machine again, and the fatigue test was performed on the specimens for fatigue test. In the graph in FIG. 21, data before their fatigue crack growth arresting processes are indicated with dotted lines, and data after the fatigue crack growth arresting processes are indicated with solid lines.

In the specimen for fatigue test of the comparative example subjected to no fatigue crack growth arresting process, the length of the one fatigue crack from the center of the hole exceeded 35 mm when the number of cycles reached approximately 620 thousand, and was eventually broken. With regard to the specimens for fatigue test subjected to the fatigue crack growth arresting process of Comparative Example A using the stop holes, one whose fatigue test conditions included the maximum tensile stress (nominal stress) Fmax at 90 MPa and the minimum tensile stress Fmin at 0 MPa was broken when the number of cycles after the provision of the stop-holes reached approximately 570 thousand, and the other whose fatigue test conditions included the maximum tensile stress (nominal stress) Fmax at 120 MPa and the minimum tensile stress Fmin at 0 MPa was broken when the number of cycles after the provision of the stop-holes reached approximately 150 thousand.

In contrast to this, the specimen for fatigue test subjected to the fatigue crack growth arresting process of Example A was broken when the number of cycles reached approximately 1.8 million. With regard to the specimens for fatigue test subjected to the fatigue test growth arresting process of Example B, one was broken when the number of cycles reached approximately 1.5 million whereas the other kept the length of the one fatigue crack from the center of the hole 52 almost unchanged from before the fatigue crack growth arresting process even after the number of cycles exceeded 5 million.

Furthermore, after the fatigue test, the external appearance around the studs was checked on each of the specimens for fatigue test subjected to the fatigue crack growth arresting processes of the example and Examples A, B. No fatigue cracks starting at the vicinities of the holes 18a, 18b into which the studs were press-fitted were observed.

The results of the fatigue tests have made it clear that the fatigue crack growth was arrested in each of the specimens for fatigue test subjected to the fatigue crack growth arresting processes of the example and Examples A, B, unlike in the specimen for fatigue test of the comparative example subjected to no fatigue crack growth arresting process, and unlike in the specimens for fatigue test subjected to the fatigue crack growth arresting process of Comparative Example A using the stop-holes.

Accordingly, it has been found that the fatigue crack growth could be arrested by providing the holes into which to press-fit the studs as the press-fit objects on the sides to the crack extension direction of each fatigue crack at its tip, for example in a way that the center of each hole was situated near the fatigue crack in the direction orthogonal to the crack extension direction of the fatigue crack at its tip.

Thereafter, evaluation was made on the effectiveness of a fatigue crack growth arresting process where tapered pins were used for the press-fitting.

First of all, descriptions will be provided for the fatigue crack growth arresting process of Example C using the tapered pins for the press-fitting. For the fatigue crack growth arresting process of Example C, a specimen for fatigue test was used which had the same shape as the specimen for fatigue test 50 including the introduced fatigue cracks, shown in FIG. 10, used for the fatigue crack growth arresting process of the foregoing example (the rectangular specimen which was 100 mm in width, 600 mm in length and 9 mm in thickness), and which were made from the same material (mild steel; JIS SS400, SM490 and the like) as the specimen for fatigue test 50.

In addition, the fatigue cracks were introduced by using the same fatigue crack introducing method as used for producing the specimen for fatigue test 50 to be used in the fatigue crack growth arresting process of the foregoing example, except that: the maximum tensile stress (nominal stress) Fmax of the applied cyclic tensile stress F for the introduction of the fatigue cracks was set at 120 MPa; and the minimum tensile stress Fmin thereof was set at 0 MPa.

In other words, as in the case of the specimen for fatigue test 50 shown in FIG. 10, slits were introduced into the specimen for fatigue test by electro-discharge machining (with the length of each slit from the center of the hole 52 set at 4 mm, and with the length from a tip of one slit to a tip of the other slit set at 8 mm). Thereafter, the fatigue testing machine made the applied cyclic tensile stress F act on the resultant specimen for fatigue test, and thereby, each of the fatigue cracks 14 was cause to grow to a length of 15 mm from the center of the hole 52 (with the length from the tip of the one fatigue crack 14 to the tip of the other fatigue crack 14 reaching 30 mm).

Figure 22:
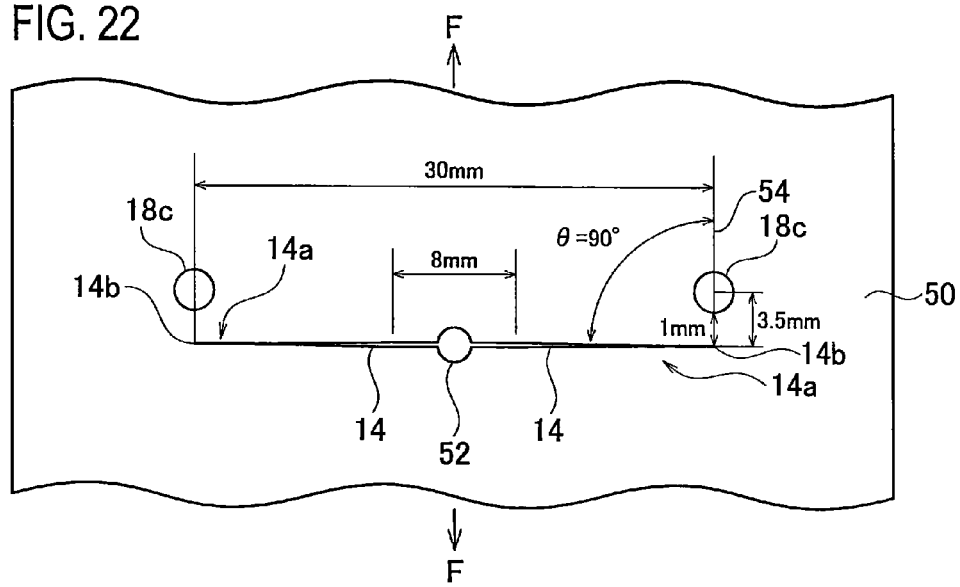
FIG. 22 is a magnified view of an area in a specimen for fatigue test including introduced fatigue cracks, where tapered holes into which to press-fit tapered pins were formed for a fatigue crack growth arresting process of Example C in the embodiment of the present invention.
Figure 23:
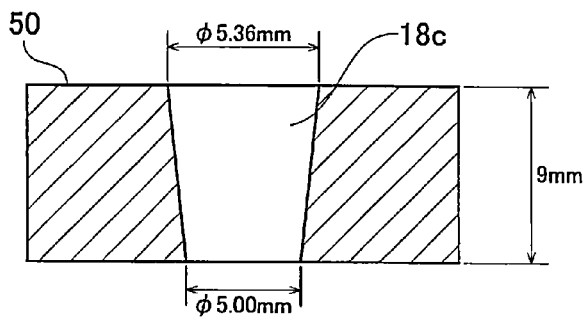
FIG. 23 is a cross-sectional view showing the shape of the tapered hole in the embodiment of the present invention.

For the fatigue crack growth arresting process of Example C, the holes into which to press-fit the tapered pins were formed into tapered holes. FIG. 22 is a magnified view of an area in the specimen for fatigue test 50 including the introduced fatigue cracks 14, where the tapered holes 18c into which to press-fit the tapered pins were formed for the fatigue crack growth arresting process of Example C. Meanwhile, FIG. 23 is a cross-sectional view showing the shape of each tapered hole 18c.

The tapered holes 18c were formed, by being drilled with a taper pin drill, in the specimen for fatigue test 50 including the introduced fatigue cracks 14. For the fatigue crack growth arresting process of Example C, the tapered holes 18c into which to press-fit the tapered pins were formed in a way that a straight line 54 joining the center of each tapered hole 18c and a tip 14b of the corresponding fatigue crack is orthogonal to the crack extension direction of the fatigue crack 14. In other words, the center of the tapered hole 18c was situated on the line extending in a direction 54 orthogonal to the crack extension direction of the fatigue crack at the tip 14b. The shortest distance between the peripheral edge of the tapered hole 18c and the tip 14b of the fatigue crack was set at 1 mm. The length of a perpendicular line to the tip 14b of the fatigue crack from the center of the tapered hole 18c was set at approximately 3.5 mm. In addition, regarding the shape of the tapered hole 18c, a large end hole diameter was set at 5.36 mm, and a small end hole diameter was set at 5.00 mm.

Two tapered holes 18c in total were formed by providing: one tapered hole 18c lateral to the crack extension direction at the tip 14b of tone of the fatigue cracks on one side of the hole 52; and the other tapered hole 18c lateral to the crack extension direction at the tip 14b of the other one of the fatigue cracks on the other side of the hole 52.

Figure 24:
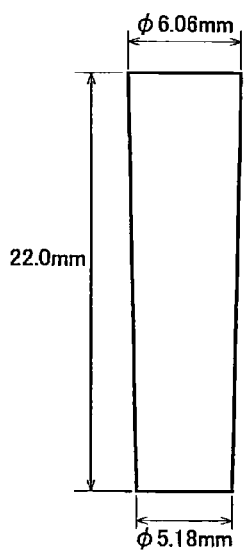
FIG. 24 is a cross-sectional view showing the shape of the tapered pin in the embodiment of the present invention.

Subsequently, each tapered pin was press-fitted into the corresponding tapered hole 18c with a hammer. FIG. 24 is a cross-sectional view showing the shape of the tapered pin. Each tapered pin was made from an alloy tool steel SKD11 and formed into a conical shape. Regarding the shape of the tapered pin, the diameter of a large end portion was set at 6.06 mm; the diameter of a small end portion was set at 5.18 mm; and its length was set at 22.0 mm. Here, one specimen for fatigue test subjected to the fatigue crack growth arresting process of Example C was produced.

Before the fatigue test, a stress analysis using the finite element method (FEM) was performed on how the tip portion 14a of the fatigue crack 14 was affected when the tapered pin was press-fitted. The stress analysis was performed by simulating the press-fitting of the tapered pin into the tapered hole with the shape shown in FIG. 24, while setting the tapered hole smaller by 0.5 mm than the pin diameter of the tapered pin.

Figure 25:
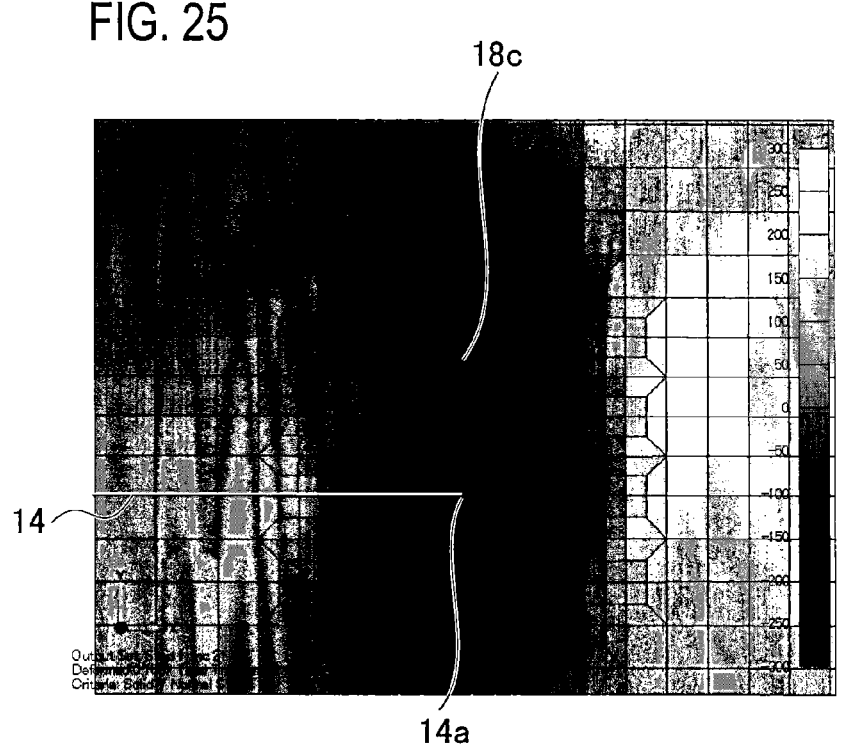
FIG. 25 is a diagram showing distribution of stress in the longitudinal direction of the specimen for fatigue test in association with press-fitting of the tapered pin was press-fitted in the embodiment of the present invention.

FIG. 25 is a diagram showing the distribution of stress in the longitudinal direction of the specimen for fatigue test 50 associated with the press-fitting of the tapered pin. A grayscale represents the level of stress acting around the tip portion 14a of the fatigue crack 14. Like in FIG. 12, the grayscale indicates that: the tensile stress is larger in a region where white is emphasized more; and the compressive stress is larger in a region where black is emphasized more. It was confirmed that: the compressive stress acted on the tip portion 14a of the fatigue crack 14 in directions lateral to the crack extension direction; and the opening of the tip portion 14a of the fatigue crack 14 was pressed.

Figure 26:
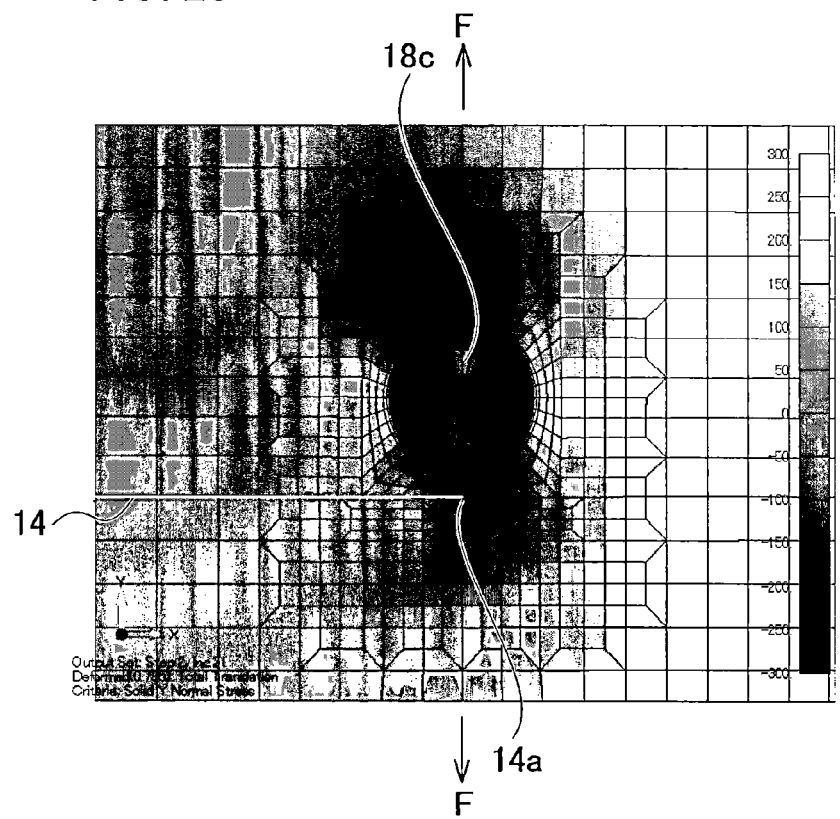
FIG. 26 is a diagram showing distribution of stress in the longitudinal direction of the specimen for fatigue test which occurred when uniform tensile stress was made to act on the specimen for fatigue test after the tapered pin was press-fitted in the embodiment of the present invention.

Subsequently, after the tapered pin was press-fitted, another stress analysis using the finite element method (FEM) was performed on the distribution of stress which occurred when uniform tensile stress was made to act on the specimen for fatigue test 50 in its longitudinal direction. FIG. 26 is a diagram showing the distribution of stress in the longitudinal direction of the specimen for fatigue test 50 which occurred when the uniform tensile stress was made to act on the specimen for fatigue test 50 after the tapered pin was press-fitted. The tensile stress made to act uniformly on the specimen for fatigue test 50 in its longitudinal direction was set at 150 MPa as nominal stress. The grayscale represents the level of stress acting around the tip portion 14a of the fatigue crack 14. Like in FIG. 12, the grayscale indicates that: the tensile stress is larger in a region where white is emphasized more; and the compressive stress is larger in a region where black is emphasized more.

It was confirmed that: even when the uniform tensile stress was made to act on the specimen for fatigue test 50, the compressive stress acting in the directions lateral to the crack extension direction remained on the tip portion 14a of the fatigue crack 14; and the opening of the tip portion 14a of the fatigue crack 14 remained pressed and closed.

A fatigue test was performed in atmosphere at room temperature on the specimen for fatigue test subjected to the fatigue crack growth arresting processes of Example C. As fatigue test conditions for the specimen for fatigue test subjected to the fatigue crack growth arresting process of Example C, the maximum tensile stress (nominal stress) Fmax was set at 120 MPa, and the minimum tensile stress Fmin was set at 0 MPa. The frequency of the fatigue test was set at 5 Hz. In addition, the length of the fatigue crack was measured with a crack gauge.

Figure 27:
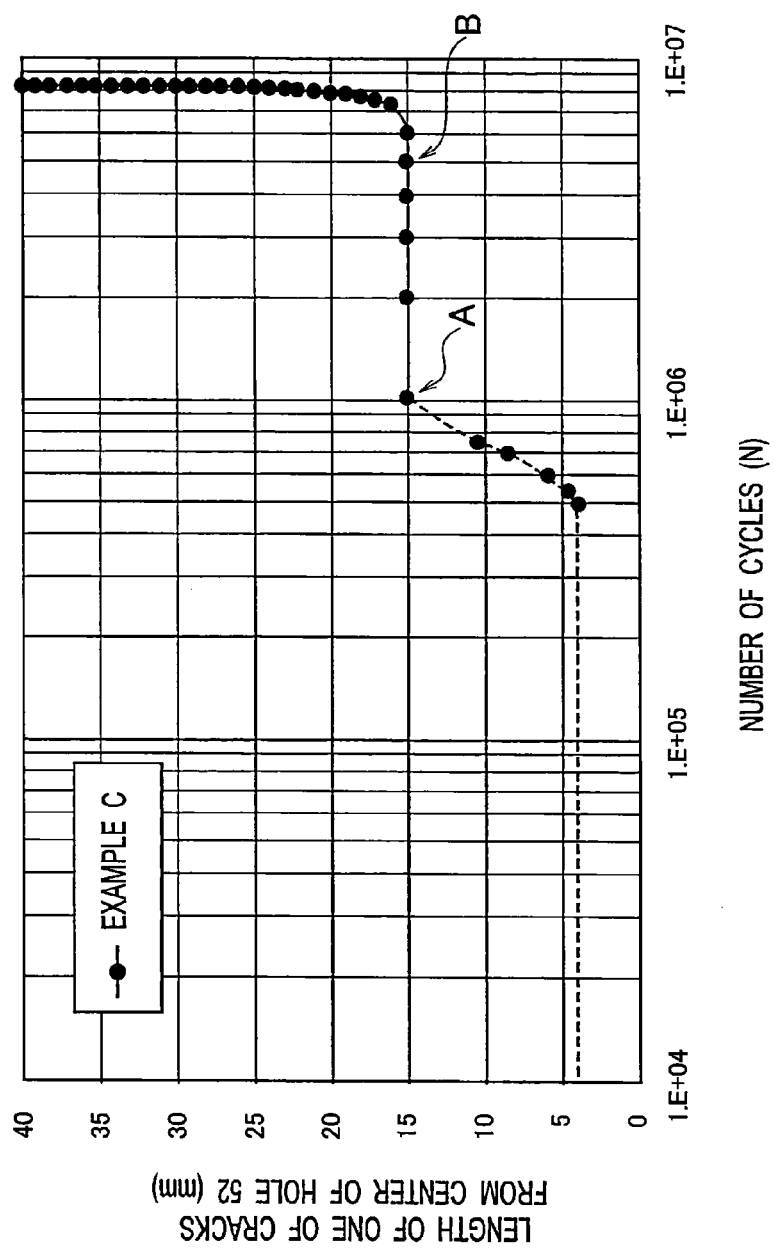
FIG. 27 is a diagram showing a result of a fatigue test in the embodiment of the present invention.

FIG. 27 is a diagram showing a result of the fatigue test. In the graph in FIG. 27, the horizontal axis represents the number (N) of cycles; the vertical axis represents the length (mm) of the fatigue crack on the one side from the center of the hole 52; and data on the specimen for fatigue test subjected to the fatigue crack growth arresting process of Example C are plotted thereon with black circles.

In addition, the graph in FIG. 27 incorporates the data on the specimen for fatigue test in the course of the fatigue crack introduction preceding the fatigue crack growth arresting process. As described above, in the specimen for fatigue test subjected to the fatigue crack growth arresting process of Example C, the one of the fatigue cracks from the center of the hole 52 was caused to grow up to a length of 15 mm in advance. After that time (in the graph in FIG. 27, a point A of time when the number of cycles reached approximately one million for the specimen for fatigue test subjected to the fatigue crack growth arresting process of Example C), the specimen for fatigue test was detached from the fatigue testing machine, and was subjected to the fatigue crack growth arresting process of Example C. Thereafter, the specimen for fatigue test subjected to the fatigue crack growth arresting process was attached to the fatigue testing machine again, and the fatigue test was performed on the specimen for fatigue test. In the graph of FIG. 27, data before the fatigue crack growth arresting process are indicated with a dotted line, and data after the fatigue crack growth arresting process are indicated with a solid line.

The specimen for fatigue test subjected to the fatigue crack growth arresting process of Example C kept the length of the one fatigue crack from the center of the hole 52 almost unchanged from before the fatigue crack growth arresting process, even after the number of cycles exceeded approximately 5 million. For this reason, the fatigue test was continued by changing the maximum tensile stress (nominal stress) Fmax to 150 MPa at a point B of time after the number of cycles exceeded approximately 5 million. The specimen for fatigue test was eventually broken after the number of additional cycles exceeded about 2270 thousand. It was found that, as described above, the fatigue crack growth could be arrested even when the tapered pins were used as the press-fit objects.

In a metal member in which a fatigue crack occurs due to the action of applied cyclic tensile stress, the present invention enables compressive stress to act on the tip portion of the fatigue crack from a direction lateral to the crack extension direction, and accordingly makes it possible to inhibit the fatigue crack propagation in the metal member. For this reason, the present invention is useful for metal members used in bridges, ships, cranes and the like.

What is claimed is:

1. A method of arresting fatigue crack growth in a metal member, comprising:
   a hole forming step of forming a hole in a metal member body in which a fatigue crack occurs due to an action of applied cyclic tensile stress, the hole arranged beside a tip portion of the fatigue crack with respect to a crack extension direction; and
   a press-fitting step of making compressive stress act on the tip portion of the fatigue crack from a direction lateral to the crack extension direction by press-fitting a press-fit object into the hole, the press-fit object being higher in stiffness than the metal member body and larger in external size than the hole.

2. The method of arresting fatigue crack growth in a metal member according to claim 1,
   wherein in the hole forming step, the hole is formed in a way that a straight line joining the center of the hole and a tip of the fatigue crack is orthogonal to the crack extension direction.

3. The method of arresting fatigue crack growth in a metal member according to claim 1,
   wherein in the hole forming step,
   a stress concentration area caused by stress concentration on the tip portion of the fatigue crack is found beforehand, and
   the hole is formed in a location outside the stress concentration area.

4. The method of arresting fatigue crack growth in a metal member according to claim 3,
   wherein in the hole forming step,
   the hole is formed in the location around the tip portion of the fatigue crack, and between the crack extension direction and a direction at an angle $\theta$ to the crack extension direction, and
   the angle $\theta$ is given by a stress analysis.

5. The method of arresting fatigue crack growth in a metal member according to claim 4,
   wherein the angle $\theta$ is 55 degrees when uniform tensile stress is made to act in a direction orthogonal to the crack extension direction.

6. The method of arresting fatigue crack growth in a metal member according to claim 1,
   wherein in the hole forming step, the hole is formed in a location where the shortest distance between a peripheral edge of the hole and the tip portion of the fatigue crack is 1 mm or longer in order to prevent the hole and the tip portion of the fatigue crack from connecting with each other when the press-fit object is press-fitted into the hole.

7. The method of arresting fatigue crack growth in a metal member according to claim 1,
   wherein in the hole forming step, the hole is formed in each of locations symmetrical with respect to the tip portion of the fatigue crack in a direction orthogonal to the crack extension direction.

8. The method of arresting fatigue crack growth in a metal member according to claim 1,
   Wherein the fatigue crack penetrates the metal member body in its thickness direction,
   the hole is formed penetrating the metal member body in its thickness direction, and
   the press-fit object is formed with a length equal to or longer than that of the hole.

9. The method of arresting fatigue crack growth in a metal member according to claim 1,
   Wherein the press-fit object includes
   a press-fit portion to be press-fitted into the hole, and
   a head portion provided on one end side of the press-fit portion, and being larger in external size than the press-fit portion, and
   the head portion of the press-fit object is provided with any one of a flange, a screw thread and a groove.

10. A fatigue crack growth-arrested metal member, comprising:
    a hole formed in a metal member body in which a fatigue crack occurs due to an action of applied cyclic tensile stress, and provided beside a tip portion of the fatigue crack with respect to a crack extension direction; and
    a press-fit object being higher in stiffness than the metal member body and larger in external size than the hole, and configured to make compressive stress act on the tip portion of the fatigue crack from a direction lateral to the crack extension direction by being press-fitted into the hole.

11. The fatigue crack growth-arrested metal member according to claim 10,
    wherein the hole is formed in a way that a straight line joining the center of the hole and a tip of the fatigue crack is orthogonal to the crack extension direction.

12. The fatigue crack growth-arrested metal member according to claim 10,
    wherein the hole is formed in a location outside a stress concentration area caused by stress concentration on the tip portion of the fatigue crack.

13. The fatigue crack growth-arrested metal member according to claim 12,
    Wherein the hole is formed in the location around the tip portion of the fatigue crack, and between the crack extension direction and a direction at an angle $\theta$ to the crack extension direction, and
    the angle $\theta$ is given by a stress analysis.

14. The fatigue crack growth-arrested metal member according to claim 13,
    wherein the angle $\theta$ is 55 degrees when uniform tensile stress is made to act in a direction orthogonal to the crack extension direction.

\* \* \* \* \*